United States Patent
Leong et al.

(10) Patent No.: US 12,033,751 B2
(45) Date of Patent: Jul. 9, 2024

(54) SYSTEMS AND METHODS FOR OPERATIONS AND INCIDENT MANAGEMENT

(71) Applicant: SOL-X Pte. Ltd., Singapore (SG)

(72) Inventors: Alister Garry Leong, Singapore (SG); Qasim Rasul Khan, Singapore (SG); Paul Keng Teoh, Singapore (SG); Daniel Mark Alcantara, Singapore (SG); Nigel Koh Chong Hoe, Singapore (SG); Alexey Pisarev, Singapore (SG)

(73) Assignee: SOL-X Pte. Ltd., Singapore (SG)

( * ) Notice: Subject to any disclaimer, the term of this patent is extended or adjusted under 35 U.S.C. 154(b) by 107 days.

(21) Appl. No.: 17/110,320

(22) Filed: Dec. 3, 2020

(65) Prior Publication Data
US 2021/0174952 A1    Jun. 10, 2021

Related U.S. Application Data

(60) Provisional application No. 62/943,995, filed on Dec. 5, 2019.

(51) Int. Cl.
*G16H 40/63* (2018.01)
*G06N 20/00* (2019.01)
(Continued)

(52) U.S. Cl.
CPC ............. *G16H 40/63* (2018.01); *G06N 20/00* (2019.01); *H04L 67/52* (2022.05); *H04Q 9/00* (2013.01)

(58) Field of Classification Search
CPC ........ G16H 40/63; G16H 40/67; G16H 50/20; G06N 20/00; H04L 67/52; H04L 67/12; H04Q 9/00; H04Q 2209/43
See application file for complete search history.

(56) References Cited

U.S. PATENT DOCUMENTS 9,060,683 B2    6/2015    Tran
9,159,212 B1   10/2015    Hadsall et al.
(Continued)

FOREIGN PATENT DOCUMENTS

CN    104887207 A    9/2015
CN    105852824 A    8/2016
(Continued)

OTHER PUBLICATIONS

PCT/SG2020/050715 International Search Report and Written Opinion dated Mar. 10, 2021.
(Continued)

*Primary Examiner* — Amine Benlagsir
(74) *Attorney, Agent, or Firm* — Wilson Sonsini Goodrich & Rosati

(57) ABSTRACT

The present disclosure provides methods and systems for managing safety and risk in a remote workplace. The method may comprise: collecting, via a local network, data stream from one or more sensors and a user device; transmitting the data stream to an edge computing device via the local network, wherein the data stream is stored in a local database; processing, at the edge computing device, the data stream to identify a hazardous condition and a health condition of a user associated with the user device; and automatically generating a dynamic geofencing area in the remote workplace base at least in part on the hazardous condition and the health condition.

28 Claims, 24 Drawing Sheets

(51) Int. Cl.
*H04L 67/52* (2022.01)
*H04Q 9/00* (2006.01)

(56) References Cited

U.S. PATENT DOCUMENTS

| | | |
|---|---|---|
| 9,775,520 B2 | 10/2017 | Tran |
| 9,811,955 B2 | 11/2017 | Russell et al. |
| 10,275,728 B2 | 4/2019 | Makhoul |
| 10,299,101 B1* | 5/2019 | Lim .................... G08B 25/005 |
| 10,691,904 B1* | 6/2020 | Randall ............. G06V 40/1365 |
| 2009/0219160 A1 | 9/2009 | Shervey et al. |
| 2011/0037599 A1* | 2/2011 | Johnson, Jr. .......... H04W 4/023 |
| | | 340/632 |
| 2014/0247151 A1 | 9/2014 | Proud et al. |
| 2015/0035644 A1 | 2/2015 | June et al. |
| 2015/0057968 A1 | 2/2015 | Bailey |
| 2015/0073907 A1 | 3/2015 | Purves et al. |
| 2015/0120375 A1 | 4/2015 | Nelson et al. |
| 2015/0245189 A1 | 8/2015 | Nalluri et al. |
| 2016/0171633 A1 | 6/2016 | Dewalt et al. |
| 2017/0146970 A1* | 5/2017 | Joo ....................... H04W 4/021 |
| 2017/0151956 A1 | 6/2017 | Boesen |
| 2018/0174378 A1* | 6/2018 | Pauli .................... G07C 5/0808 |
| 2019/0158979 A1 | 5/2019 | Jurzak et al. |
| 2019/0188399 A1* | 6/2019 | Palaniappan ......... H04L 9/3239 |
| 2019/0236370 A1* | 8/2019 | Man .................... G06Q 10/0633 |
| 2019/0343429 A1* | 11/2019 | Elhawary ............. A61B 5/6823 |
| 2020/0029635 A1* | 1/2020 | Kiemele ............... A41D 19/015 |
| 2021/0158207 A1* | 5/2021 | Alsahlawi ................ G06N 5/04 |
| 2021/0343182 A1* | 11/2021 | Lu .......................... G09B 19/24 |

FOREIGN PATENT DOCUMENTS

| | | |
|---|---|---|
| CN | 107423900 A | 12/2017 |
| CN | 109828514 A | 5/2019 |
| GB | 2537019 B | 9/2019 |
| KR | 100886847 B1 | 3/2009 |
| WO | WO-2015025273 A1 | 2/2015 |
| WO | WO-2019212795 A1 | 11/2019 |
| WO | WO-2021112766 A1 | 6/2021 |

OTHER PUBLICATIONS

EP20896416.3 Extended European Search Report dated Dec. 19, 2023.

* cited by examiner

SYSTEMS AND METHODS FOR OPERATIONS AND INCIDENT MANAGEMENT

CROSS-REFERENCE TO RELATED APPLICATIONS

This application claims the priority and benefit of U.S. Provisional Application No. 62/943,995, filed on Dec. 5, 2019, the entirety of which is incorporated herein by reference.

BACKGROUND

Safety and risk management in the marine environment is challenging. It can encompass various aspects from regulatory compliance, operational processes administration, fatigue management to behavioral cultivation of the operators or personnel onboard a large vessel. The conventional safety approach deployed in a marine context may rely on paper documents which can cause clerical overload, procedural compliance mistakes, lack of real-time monitoring and capability of enforcing safety laws.

SUMMARY

Recognized herein is a need for methods and systems for managing safety and risk in a hazardous workplace with improved efficiency and accuracy. The present disclosure provides systems and methods for managing safety and risk of personnel performing operations in hazardous environments. In particular, the provided systems and methods may improve compliance of safety processes and workflow administration onboard vessels, floating structures and systems (e.g., cargo ships, tankers, cruise ships or any other water-borne vessels).

Systems and methods of the present disclosure provide an integrated platform for controlling work flow, detecting, predicting and managing risks in the maritime industry. In some cases, the provided systems and methods may help vessel operators to comply with safety laws or maritime laws, improve crew situational awareness for hazardous environments and conditions, enforce pro-active safety behaviors based on real-time tracking and situation detection, and provide a single access-point for all audit and survey documents and data. The provided systems and methods may be capable of integrating on-the-job workflows with data from the physical world (e.g., edge information such as location, time, temperature, etc.), and generating multi-dimensional contextual information based on the integrated workflow and aggregated data. The multi-dimensional contextual information may allow users to view or access the aggregated contextual information along multiple dimensions, such as what work was done, work was done by whom and at what point in time, one or more environmental/personal conditions (e.g., in high heat for an extended period of time, operator is under fatigue, etc.) under which work was performed and various other dimensions. A dimension can refer to a dimension associated with any type of contextual information extracted from the physical data and workflow. The dimensions can be orthogonal dimensions—that is, dimensions that are mutually exclusive. As an alternative, some of the dimensions can be inclusive of other dimensions. For example, the what work was done dimension can overlap at least to some extent with the work was done by whom and at what time dimension.

Example embodiments are described with reference to the tracking of personnel or operators on vessels. However, it is to be understood that the invention itself is more broadly applicable, and other example embodiments may be applied to the tracking of persons and objects generally, including, for example, on other kinds of vessels, in a workplace such as buildings, and on other properties.

In an aspect, a method for managing safety and risk in a hazardous or remote workplace is provided. The method may comprise: collecting, via a local network, data stream from one or more sensors and a user device; transmitting the data stream to an edge computing device via the local network, wherein the data stream is stored in a local database; processing, at the edge computing device, the data stream to identify a hazardous condition and a health condition of a user associated with the user device; and automatically generating a dynamic geofencing area in the remote workplace base at least in part on the hazardous condition and the health condition.

In some embodiments, the one or more sensors comprise at least one sensor located onboard the user device and at least one sensor deployed in the remote workplace. In some cases, the user device is a wearable device and the data stream collected from the at least one sensor located onboard the user device includes a heart rate of the user. For example, the data stream collected from the at least one sensor located onboard the user device further comprises an activity level of the user. In some cases, the method further comprises calculating a work and rest hour of the user based on the data stream. In some cases, the data stream collected from the at least one sensor located onboard the user device includes a temperature and humidity of the environment surrounding the user. For example, the method further comprises determining a heat stress level of the user based on the data stream.

In some embodiments, the hazardous condition is identified by processing the data stream using a machine learning algorithm trained model. In some embodiments, the hazardous condition is identified based at least in part on workflow data inputted by a user via the user device.

In some embodiments, the health condition of the user comprises a fatigue level or a heat stress level. In some embodiments, a boundary of the dynamic geofencing area is determined based at least in part on the hazardous condition and the corresponding location. In some embodiments, a permission to enter the dynamic geofencing area is determined based at least in part on the health condition of the user. In some embodiments, a permission to enter the dynamic geofencing area is determined by a supervisory user and the dynamic geofencing area is automatically terminated upon detection of an operation completed within the geofencing area. In some embodiments, the method further comprises transmitting a report comprising the identified hazardous condition and health condition to a remote entity for further analysis.

Another aspect of the present disclosure provides a system for managing safety and risk in a remote workplace or hazardous workplace. The system comprises: a local network deployed in the remote workplace; an edge computing device configured to: receive data stream from one or more sensors and a user device via the local network; process the data stream to identify a hazardous condition and a health condition of a user associated with the user device; and automatically generate a dynamic geofencing area in the remote workplace base at least in part on the hazardous condition and the health condition.

In some embodiments, the one or more sensors comprise at least one sensor located onboard the user device and at least one sensor deployed in the remote workplace. In some cases, the user device is a wearable device and the data stream collected from the at least one sensor located onboard the user device includes a heart rate of the user. For example, the data stream collected from the at least one sensor located onboard the user device further comprises an activity level of the user and the edge computing device is further configured to calculate a work and rest hour of the user based on the data stream. In some cases, the data stream collected from the at least one sensor located onboard the user device includes a temperature and humidity of the environment surrounding the user and the edge computing device is further configured to determine a heat stress level of the user based on the data stream.

In some embodiments, the hazardous condition is identified by processing the data stream using a machine learning algorithm trained model. In some embodiments, the hazardous condition is identified based at least in part on workflow data inputted by a user via the user device. In some embodiments, the health condition of the user comprises a fatigue level or a heat stress level. In some embodiments, a boundary of the dynamic geofencing area is determined based at least in part on the hazardous condition and the corresponding location. In some embodiments, a permission to enter the dynamic geofencing area is determined based at least in part on the health condition of the user. In some embodiments, a permission to enter the dynamic geofencing area is determined by a supervisory user and the dynamic geofencing area is automatically terminated upon detection of an operation completed within the geofencing area. In some embodiments, the system further comprises a local database for storing the data stream.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
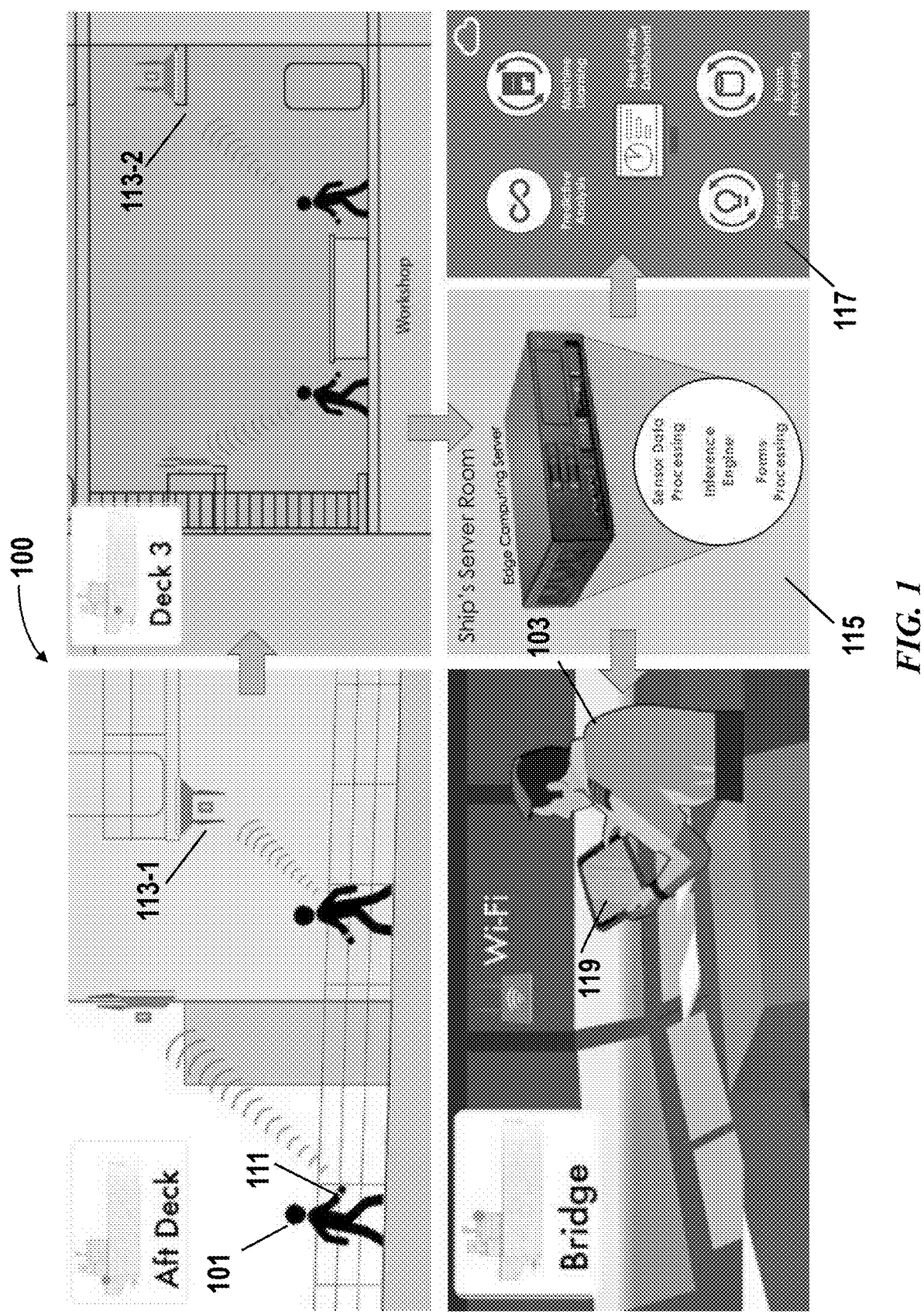
FIG. 1 schematically illustrates a safety and risk management system implemented in a maritime environment.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

A vessel can be any vehicle traversing water body. For example, a vessel can be a cargo ship, tanker, cruise ships, submarines, floating platforms, floating storage units, floating systems, or any other water-borne vessel, watercraft in marine industry. The provided safety systems and methods may be applied to various industries, worksites or workplaces. For example, the safety systems and methods can be applied to managing safety of individuals on any mobile object configured to move within any suitable environment, such as in air, in water (e.g., a ship or a submarine), on ground (e.g., a train), under the ground (e.g., a subway), in space (e.g., a spaceplane), or any combination of these environments. The provided systems and methods may be applied to the managing safety and risks of persons, for example, in a stationary environment such as buildings, factories, industrial environments and on other properties.

The provided safety systems and methods may be for use with maritime vessels which is capable of accurately determining the location and/or motion of an individual, such as a crew member, a sailor, a seaman, a mariner, or seafarer who works aboard a watercraft as part of its crew, and may work in any one of a number of different fields that are related to the operation and maintenance of a ship or a vessel.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "real-time," as used herein, generally refers to a response time of less than 1 second, tenth of a second, hundredth of a second, a millisecond, or less, such as by a computer processor. Real-time can also refer to a simultaneous or substantially simultaneous occurrence of a first event with respect to occurrence of a second event. One or more operations in the present disclosure can be performed in real-time or near real-time.

The present disclosure provides methods and systems for safety and risk management in a hazardous environment. The hazardous environment may be a remote workplace, a place where hazardous work is conducted or a mobile workplace. Methods and systems of the present disclosure can be used in various contexts, such as maritime where safety and risk assessment and management are required. For example, the present disclosure may provide situational awareness functionality, safety management workflow based on location tracking and situation detection that may be used in various contexts, including maritime (e.g., large cargo, vessel, offshore floating assets), shipping, oil & gas, industrial environments and various other industries. The real-time location tracking, behavior enforcement and situational awareness functionality of the present disclosure may be used for various uses, such as Internet of Things (IoT) platforms, health-monitoring software applications and business processes or industrial workplace management, and for organizations in energy, manufacturing, aerospace, automotive, chemical, pharmaceutical, telecommunications, healthcare, the public sector, and others.

Safety and Risk Management System

The present disclosure provides systems and methods for managing safety and risk in a hazardous workplace. In particular, the provided safety and risk management systems and methods can be applied to workflow management, safety and risk assessment related to various aspects of maritime including, for example, crew or operators' safety behavior change or guide, location tracking of crew onboard a vessel, situational awareness of lone worker hazardous work, safety law or maritime law compliance (e.g., smart step-by-step workflow, streamlined approval management process, document control for audit compliance and record management), and dealing with accidents and other events happening to the vessel or crew during operation.

In some embodiments, the safety and risk management system may be a location and/or time-based system that may utilize real-time sensor data for incident detection, location tracking, and safety behavior compliance. In some cases, the safety and risk management system can analyze data collected from one or more sensors or devices to identify a streamlined safety workflow or operation processes, capture crew-based metrics (e.g., fatigue level, health condition, under-stress, physiological state, etc.), detect an incident (e.g., trip, slip or fall detection), identify a hazardous situation or hazardous conditions in a work zone of a workplace, and identify an efficient workflow for one or more operators and one or more groups. Sensor data can be collected from wearable sensors worn by or mobile devices carried by operators or personnel performing tasks onboard a vessel. The sensor data, processed data, and related data flow may be communicated over a network suitable for use in a remote environment, such as in an area with limited wireless Internet or cellular network access, or an area without connection to a wide area network ("WAN") or an internetwork (e.g., the Internet). One or more managers, supervisors or users can monitor and view the real-time safety condition in the worksite.

FIG. 1 schematically illustrates a safety and risk management system implemented in a maritime environment 100. The safety and risk management system may be configured to automate an operation process or workflow in compliance with safety regulations, track locations of individuals 101 onboard the vessel, and detect incident and hazardous situations based at least in part on sensor data. The safety and risk management system may comprise a set of connected devices, one or more physiologic or kinematic sensors, an edge gateway (e.g., edge computing device/server) 115 for processing data collected from the above-mentioned devices or sensors and providing real-time feedback to an individual 101 or user 103, and a backend predictive model system 117. In some embodiments, the safety and risk management system may employ an edge intelligence paradigm that data processing and prediction/inference is performed at the edge or edge gateway 115 while the predictive models may be built, developed and trained on the backend predictive model system 117 residing on a cloud/data center and run on the user device (e.g., hardware accelerator) 119 and/or wearable devices 111 for inference. For instance, sensor data stream may be sent to the on-ship edge computing device 115 in real-time for managing on-ship operations, safety and risk (e.g., while the vessel is in motion), whereas a message package comprising batch data may be sent to a fleet manager or the cloud (e.g., while the vessel or cruise ship returns to the port or seashore or close to the seashore) at a lower frequency.

In some cases, at least part of the safety and risk management system may be deployed in a remote or hazardous worksite such as a large vessel. The worksite on a large vessel may have limited wireless Internet or cellular network access particularly when the vessel is in a remote area (e.g., sea) that is remote from a wide area network ("WAN") or an inter-network (e.g., the Internet). The maritime worksite may have indoor and outdoor area or work zones where operations, tasks and duties are performed. For example, the worksite may comprise bridge deck, upper deck, engine control room (ECR), steering gear room and various other indoor or outdoor work zones.

Operations or tasks performed by one or more individuals 101 (e.g., crewmembers, operators) may be tracked and guided based on real-time sensor data and feedbacks. In some embodiments, at least part of the sensor data may be captured by one or more sensors from a user's electronic device, such as a mobile device, user's wearable device, and the like.

An individual 101 (e.g., crewmember, operator, worker) may be associated with one or more sensors. In some cases, an individual may be associated with one or more types of sensors that can be located on the individual's body (e.g., attached to skin), a part of body (e.g., wearable device 101) or clothing. In some cases, the one or more types of sensors may be located remotely from an individual, such as deployed in an environment (e.g. wall-mounted, attached to the deck) or located on a user device. Examples of user devices may include, but are not limited to, mobile devices, smartphones/cellphones, tablets, personal digital assistants (PDAs), laptop or notebook computers, desktop computers, media content players, virtual reality systems, augmented reality systems, or microphones. The user device may be any electronic device capable of analyzing, receiving user input data (e.g., receiving user input for an incident report or emergency alert, user input to complete a smart form, etc.), providing or displaying certain types of feedback data (e.g., adverse event statistics, alert, behavior change cue, etc.) to a user.

The one or more sensors may comprise various types of sensors such as physiologic sensors, kinematic sensors, audio sensors and the like. Examples of types of sensors may include inertial sensors (e.g., accelerometers, gyroscopes, and/or gravity detection sensors, which may form inertial measurement units (IMUs)), location sensors (e.g., global positioning system (GPS) sensors, mobile device transmitters enabling location triangulation), heart rate monitors, external temperature sensors, skin temperature sensors, skin conductance, neural signals (e.g. EEG), muscle signals (e.g. EMG), capacitive touch sensors, sensors configured to detect a galvanic skin response (GSR), vision sensors (e.g., imaging devices capable of detecting visible, infrared, or ultraviolet light, such as cameras), proximity or range sensors (e.g., ultrasonic sensors, lidar, time-of-flight or depth cameras), altitude sensors, attitude sensors (e.g., compasses), pressure sensors (e.g., barometers), humidity sensors, vibration sensors, audio sensors (e.g., microphones), and/or field sensors (e.g., magnetometers, electromagnetic sensors, radio sensors). In some cases, the user device or the sensors may be capable of delivering an alert (e.g., vibration, audio alarm, etc.) in response to a detection of an incident (e.g., trip, fall), an intervention for changing behavior (e.g., fatigue detection or heat exhaustion) or forecasting a hazardous situation (e.g., prediction of an impeding adverse event in a work zone or a physiological condition of the individual). For example, upon the prediction of an impending adverse event (e.g., entering a hazarders work zone, reaching a fatigue level, etc.), intervention such as rhythmic cue, audio, visual, or tactile stimulus may be delivered to the crewmember via the user device, wearable device or sensors.

As described above, in some cases, the safety and risk management system may comprise sensors deployed in various locations onboard the vessel for detecting a hazardous situation or adverse event in the environment. A worksite can have various regions or work zones which can be associated with one or more sensors deployed therein. Such sensors can include, for example, the navigation system, sensors onboard the vessel such as laser imaging detection and ranging (Lidar), radar, sonar, differential global positioning system (DGPS), inertial measurement unit (IMU), gyroscopes, magnetometers, accelerometers, ultrasonic sensors, image sensors (e.g., visible light, infrared), heat sensors, audio sensors, vibration sensors, conductivity sensors, chemical sensors, biological sensors, radiation sensors, conductivity sensors, proximity sensors, or any other type of sensors, or combination thereof. The one or more sensors deployed on the vessel may be used to detect ambient environment condition in a work zone, and/or work in conjunction with the sensor or user devices for location and time-based tracking, incident detection, and providing situational awareness to the individuals.

Network Configuration

Data captured by the sensors, wearable device, user devices, as well as real-time feedback data and workflow management data may be communicated via a customized network architecture well-suited for use in a remote environment. In some cases, the network architecture may comprise a local network that is on-ship or onboard the vessel. The local network may employ a topology or configuration capable of operating in challenging environments where obstructions or distance prevent wireless communication from a device to a hub. For example, the local network may employ industrial grade WiFi Mesh technology providing stronger and more reliable Wi-Fi signals. Alternatively or in addition to, the local network may be a mesh network where devices communication with each other without a centralized device, such as a hub, switch or router. Details about the local network are described later herein.

The network architecture may comprise interconnect infrastructure or fabric such as purpose-built hardware, herein referred to as "gateways," which are compatible with a wireless protocol. The local (e.g., on-ship) network may have static configuration or dynamic configuration as described above, and the real-time data may be transmitted to an edge computing system 115 for analysis. The edge computing system 115 may be onboard the vessel. The edge computing device 115 may be in communication with a remote cloud/data center 117 through the gateways for downloading trained predictive models, and transmitting data such as fleet data (e.g., data from the on-shore operating system, data collected onboard the vessel) and various others. For instance, sensor data stream may be transmitted to the on-ship edge computing system 115 in real-time for managing on-ship operations, safety and risk (e.g., while the vessel is in motion), whereas a message package comprising batch data may be sent to a fleet manager or cloud (e.g., while the vessel or cruise ship returns to the port or seashore) at a lower frequency. Details about the predictive model system and edge computing system are described later herein.

Figure 2:
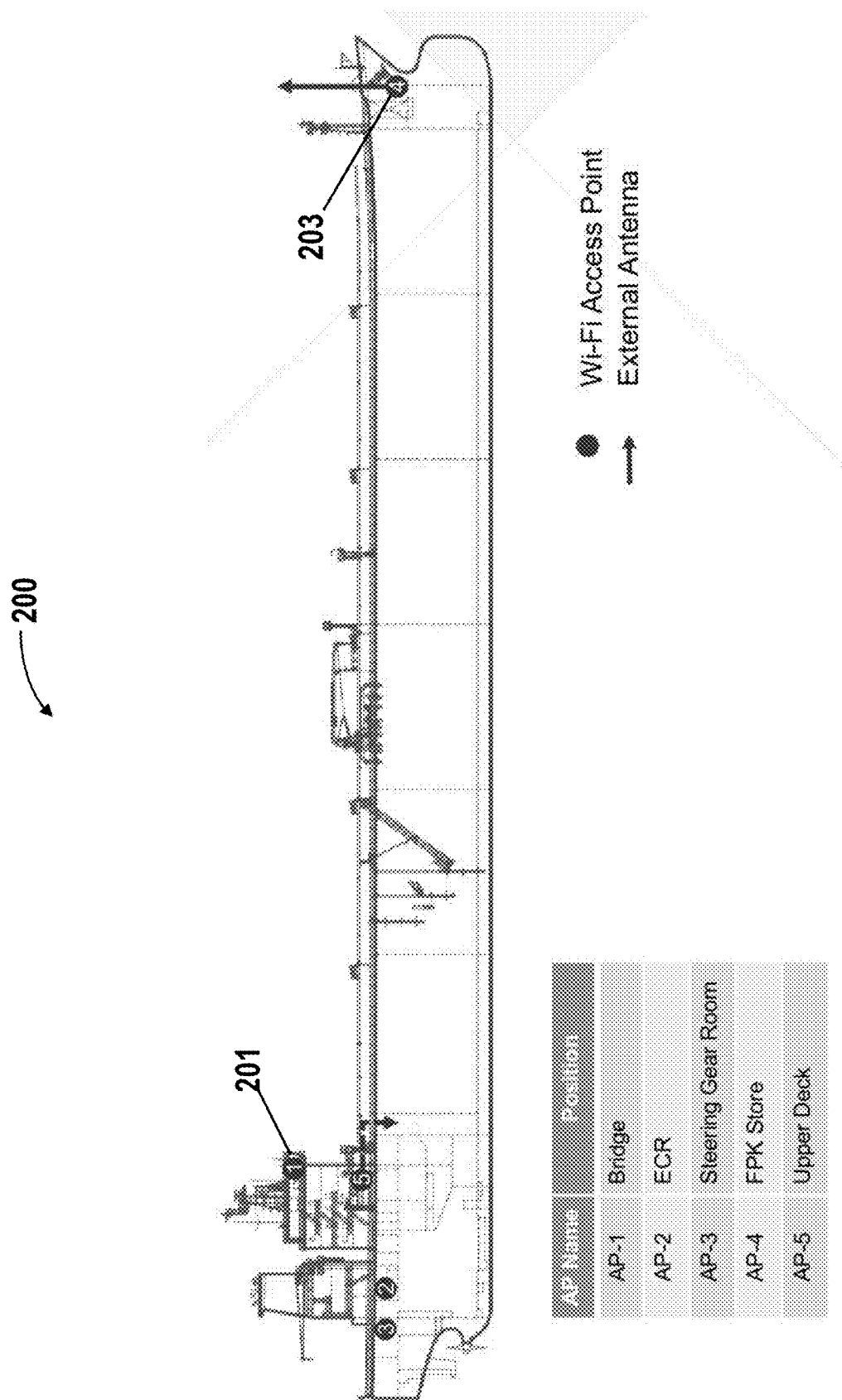
FIG. 2 shows an example configuration of a local network onboard a vessel, in accordance with some embodiments of the invention.

FIGS. 2-5 show various example configurations of a local network. The local network may be an on-ship network comprising a set of connected devices onboard a vessel. In some embodiments, the local network may comprise a WiFi-beacon configuration. As shown in FIG. 2, the network 200 may be a wireless network and the network configuration may comprise one or more WiFi Mesh access points 201 or 203 and one or more beacons deployed on the vessel. The network of devices may be deployed to provide full network coverage at the worksite or on the vessel. In some cases, the deployment of the network devices may be determined based on the layout (e.g., indoor/outdoor layout) of the vessel or work zone (e.g., location where tasks to be performed) of the vessel such that a reliable network coverage is provided in the workplace. The plurality of sensors worn by the individuals or user devices carried by an individual may be in communication with the on-ship edge computing device and/or a remote entity (e.g., cloud) via the wireless network. The WiFi Mesh access points 201 or 203 can be deployed in various locations on the vessel thereby providing network coverage in all the work zones including the highly hazardous zones. As shown in the example, the WiFi Mesh access points can be deployed in an indoor location such as the steering gear room, or outdoor location such as upper deck. In some cases, the network 200 may comprise a communication unit such as a WiFi controller or switch responsible for deciding a data path or data link according to a routing table. The network 200 may also comprise a gateway 203 connecting the local network 200 to a remote network or network entity (e.g., cloud).

The gateway device 203 may provide long range RF wireless coverage (e.g., DLPWAN) to connect the local network (e.g., on-ship network). The gateway devices may allow long range communications. In some cases, the long-range RF wireless coverage may be a narrowband wireless network coverage. In some cases, data transmission between the local network and the cloud through the gateway may be performed according to a data transmission scheme taking into account the geolocation of the vessel. Details about the data transmission scheme are described later herein. A single gateway device may each support many of the one or more onboard devices (e.g., wearable devices, edge computing server, mobile devices, etc.) on the local network. In some cases, the gateway devices may have an operating range of up to one kilometer (km). In some cases, the gateway devices may employ any suitable coding or modulation scheme such as binary shift keying (BSK), direct sequence spread spectrum (DSSS), frequency hopping spread spectrum, or Gauss frequency-shift keying (GFSK), Quadrature Amplitude Modulation (QAM) or quadrature phase shift keying (QPSK), power amplification, forward error correction (FEC) and, various other data transmission methods. In some cases, the gateway devices may switch power amplification, bandwidth, and/or bitrate in real-time to optimize for signal quality, transmission rate, and/or battery life.

In some cases, the gateways may connect to a wide area network (e.g., Internet) or cloud using any TCP/IP or UDP-based capable backhaul, such as Ethernet, Wi-Fi or cellular. The gateways may contain a radio frontend capable of listening to several MHz of RF wireless spectrum at a time, and/or configured to hear all network traffic transmitted within that spectrum. In some cases, the gateways may use synchronized frequency hopping schemes.

In some cases, a geo-location of the gateways may be detected and tracked. In some cases, the geo-location of the gateways may be used to determine a data transmission schedule. For example, when the gateway is a long distance away from the seashore, data may be transmitted from the vessel to the cloud at a lower frequency. Details about the data transmission between the local network and the cloud are described later herein. The gateways can require a GPS or GNSS transceiver to obtain accurate position and/or date/time information.

Figure 3A:
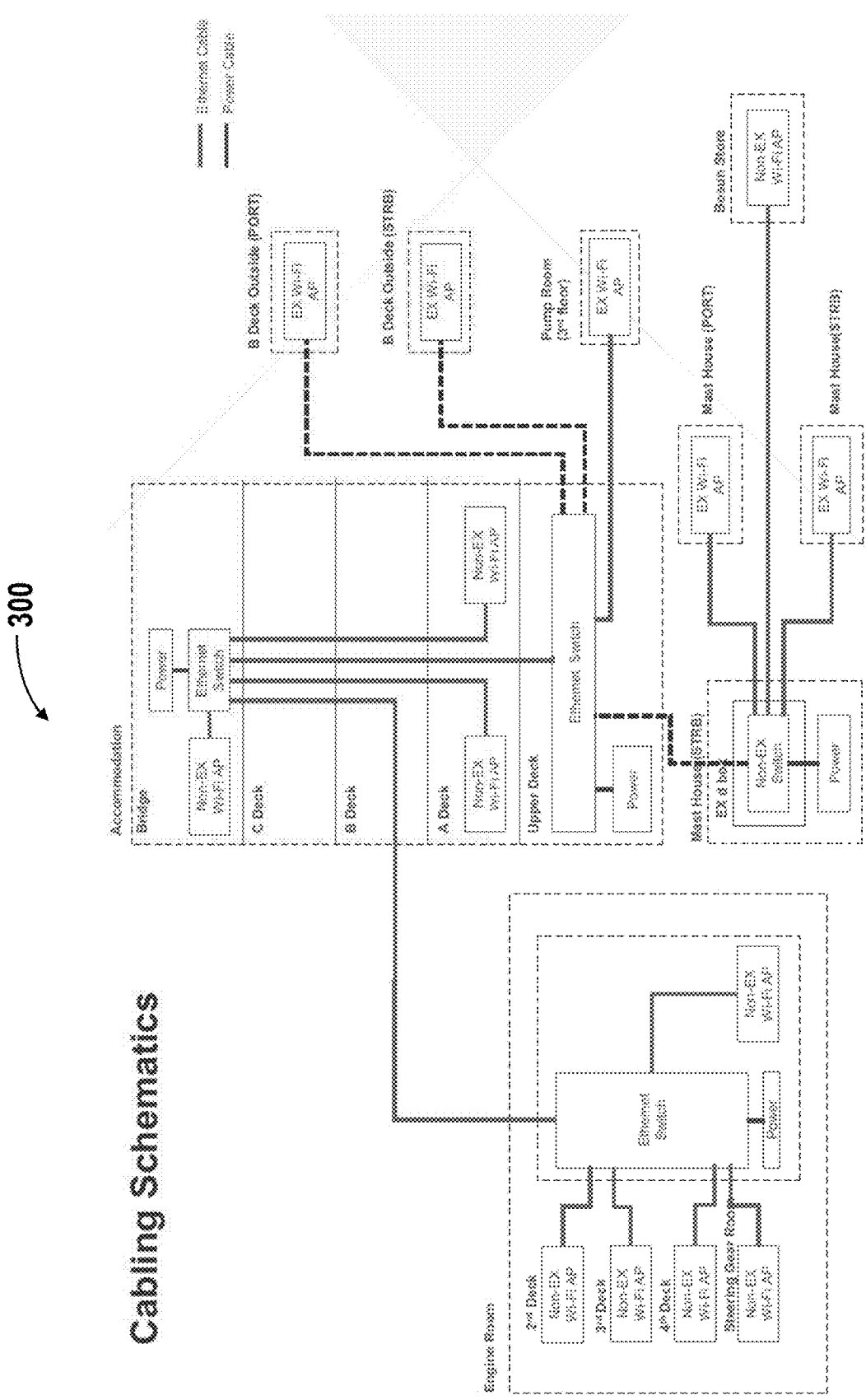
FIG. 3A shows an example of a Wi-Fi network deployed onboard a vessel, in accordance with some embodiments of the invention.
Figure 3B:
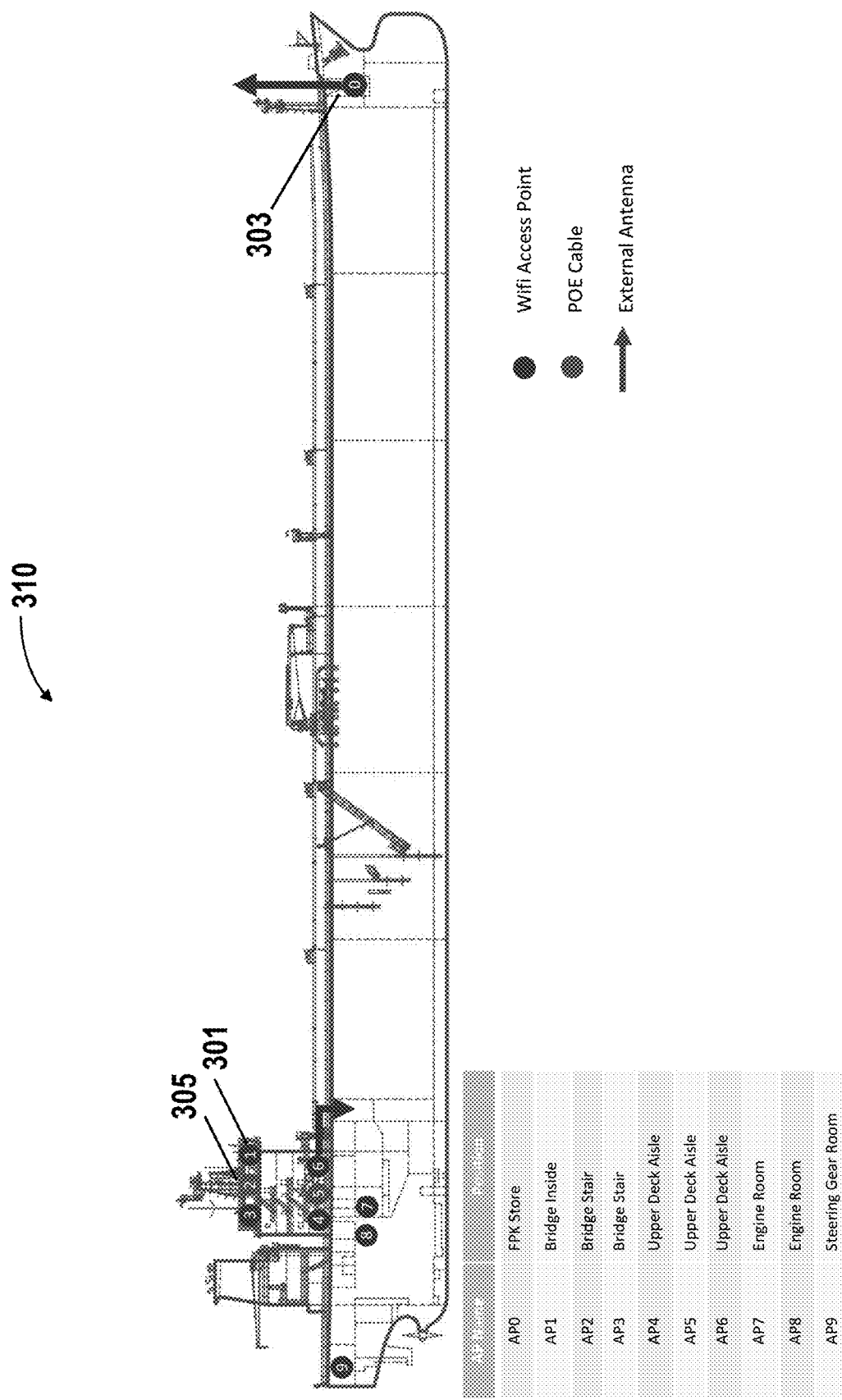
FIG. 3B shows an example network configuration on a vessel.
Figure 3C:
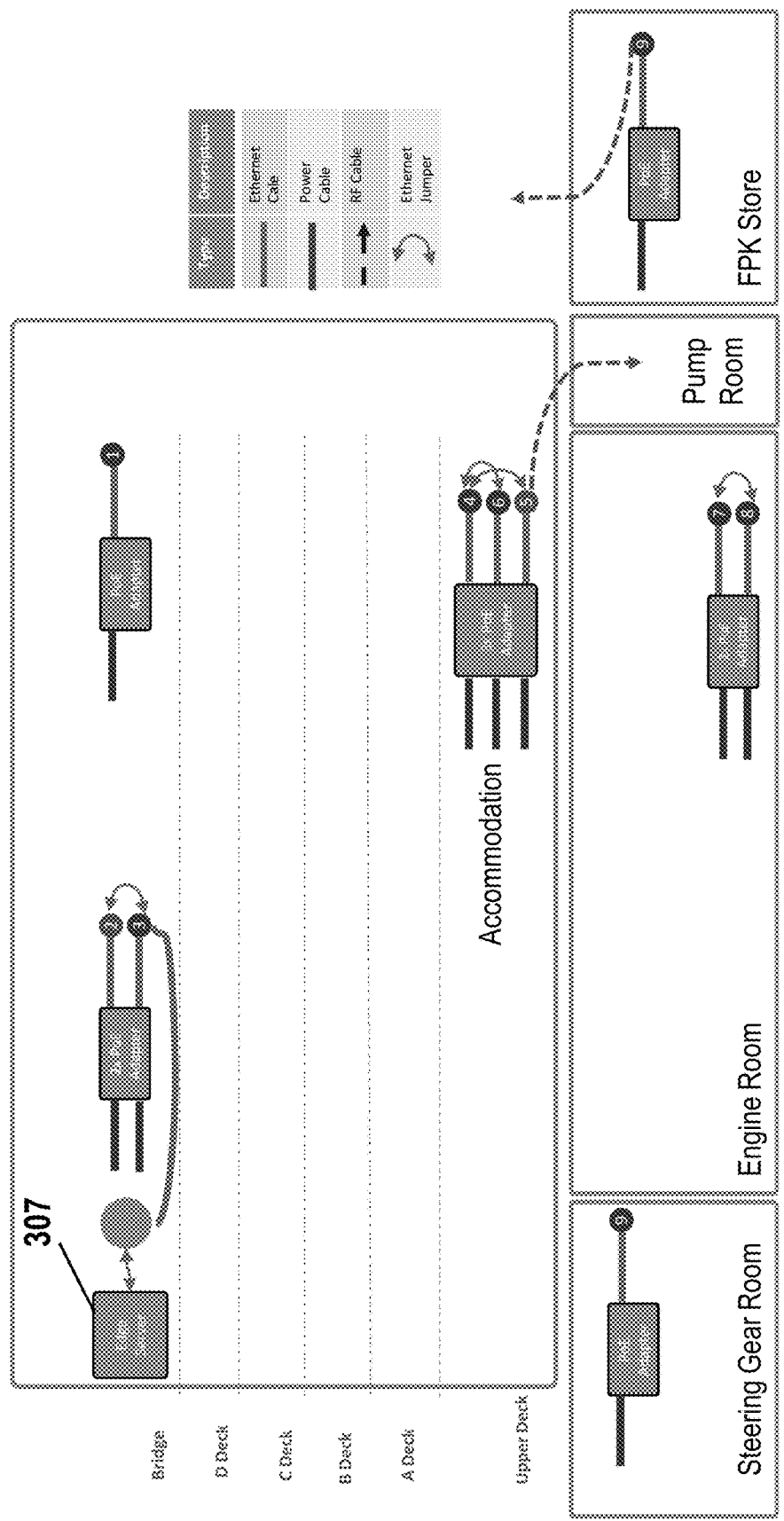
FIG. 3C shows another view of the Wi-Fi network deployed on the vessel.

In some embodiments, the local network may be a combination of wired and wireless network. In some embodiments, the network configuration may comprise a plurality of Wi-Fi access points connected to a plurality of network switches or hubs (e.g., Ethernet switch), and one or more beacons. FIG. 3A shows an example of the Wi-Fi network 300 deployed onboard a vessel. One or more Wi-Fi access points may be cable wired to one or more Ethernet switches. The Wi-Fi access points and switches can be deployed in various locations on the vessel. As shown in the example, the Wi-Fi access points and switches can be deployed in an indoor location such as inside an engine room, Bosun Store, pump room, or outdoor location such as outside upper deck or in the accommodation tower. The deployment of the Wi-Fi access points may be designed such that a full network coverage is provided to the work zones on the vessel. The switches or Wi-Fi controllers may be responsible for deciding a data path or data link according to a routing table. The plurality of network switches may be wire/cable connected to a power source. The network 300 may also comprise a gateway such as the IS (Internet service) Wi-Fi access point to connect the local network 300 to a remote network (e.g., Internet) or network entity (e.g., cloud). FIG. 3B shows another example network configuration 310 comprising one or more WiFi Mesh access points 301, 303, PoE cables 305 for connecting one or more Wi-Fi access points to one or more Ethernet switches, and one or more beacons deployed on the vessel. FIG. 3C shows another view 320 of the Wi-Fi network deployed on the vessel. As shown in the example, the edge server 307 is located at the bridge and is in connected to various components/devices onboard the vessel through the combination of the wired and wireless network.

Figure 4:
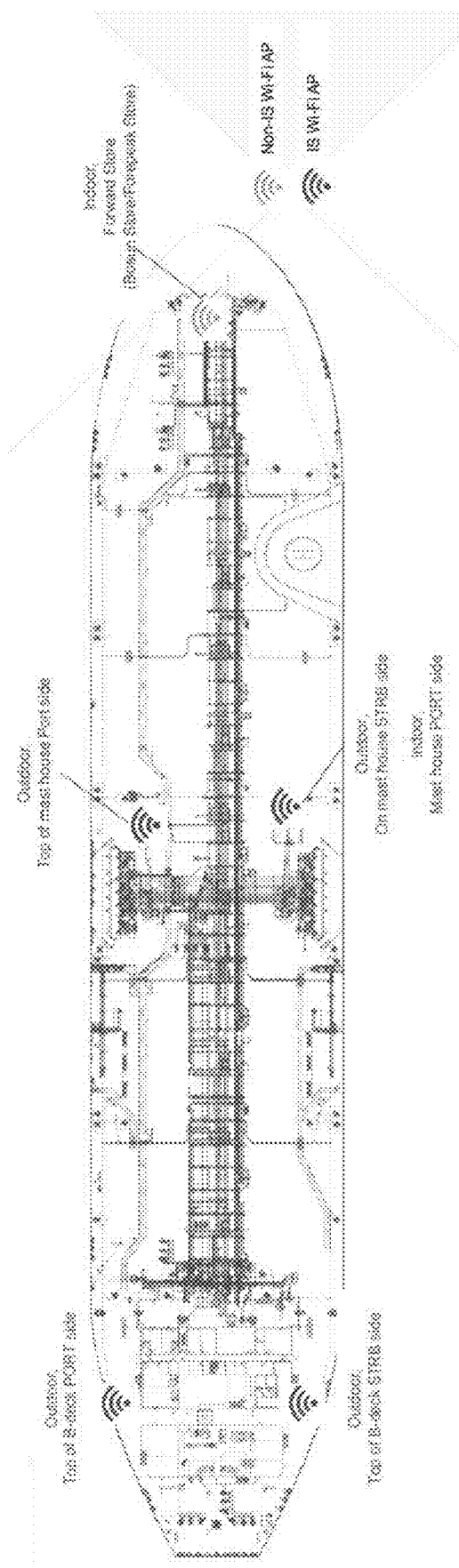
FIG. 4 shows an example deployment that a plurality of Wi-Fi access points located in various outdoor locations onboard a vessel, in accordance with some embodiments of the invention.

FIG. 4 shows an example deployment that a plurality of Wi-Fi access points located in various outdoor locations onboard a vessel. For example, the plurality of Wi-Fi access points can be mounted to the top of B-deck PORT side, the top of B-deck mast house (STRB) side and the like.

Figure 5:
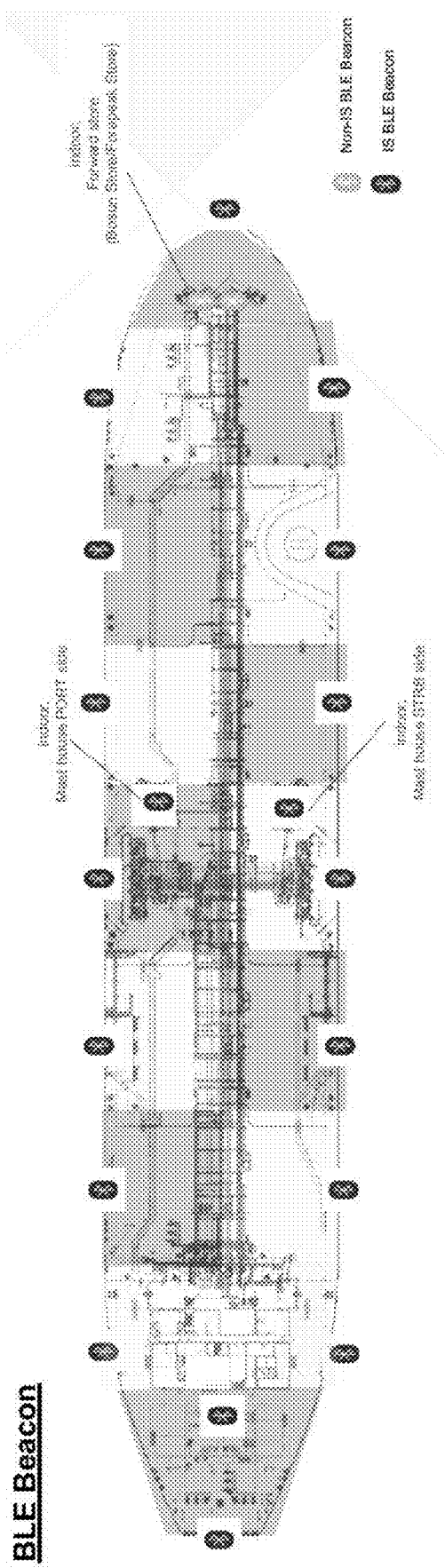
FIG. 5 shows an example deployment of wireless radio transmitters on a vessel.

In some embodiments, the local network may also comprise a plurality of devices such as Beacon devices for indoor/outdoor positioning or wireless communication. In some cases, the local network may allow for indoor/outdoor position tracking, such as populating the indoor/outdoor space with Bluetooth Low Energy (BLE) beacons that transmit a continuous stream of packets that are picked up by a BLE sensor on the mobile device or the wearable device. FIG. 5 shows an example deployment of wireless radio transmitters (e.g., BLE sensors) on a vessel. As shown in the example deployment, a plurality of Beacon devices may be placed in various indoor locations on a vessel. This may beneficially improve the indoor position tracking of an individual. For instance, with BLE, a position of mobile devices or wearable devices can be identified based on the proximity technology. The proximity technology for users may include a plurality of beacons distributed about a premise through which the user is located or to navigate. The user device such as the mobile device or wearable device may be BLE compatible so as to determine the user's relative physical location to a beacon. Based on ranging data or approximate distance between user's device to each beacon along with the unique beacon's properties, different level of positioning accuracy can be achieved. For instance, the proximity technology may determine the location of a wearable device or user device based on a proximity estimate of signal strength emitting from beacon. In addition, it can be enhanced with a beacon triangulation method to determine the (x, y, z) local map coordinates of user's indoor position referencing to three or more beacons in proximity. The receiver can estimate its position using average of x,y,z localized coordinates of a floor map for e.g. (x1, y1, z1), (x2, y2, z2) and (x3, y3, z3).

It is noted that the local network can have various other configurations or utilize other suitable techniques. For example, instead of or in addition to Beacons, proximity sensors such as LIDAR reflective markers, radio or RFID beacons, GPS beacons, wireless location beacons, or other reference features may be provided within an indoor area. The reference features may include visually discernible markers, IR-discernible markers, UV-discernible markers, and/or beacons that may emit a wireless signal. The user device or wearable device may be equipped with the corresponding sensors (e.g., LIDAR, camera) to track the location of an individual relative to the location of the reference features.

Additionally, the network configuration may be dynamic. For example, one or more of the network devices may not be stationary relative to the vessel. In another example, the network configuration may be dynamically changing. In some cases, the local network may be a mesh network. In a mesh network, devices communication with each other without a centralized device, such as a hub, switch or router. In some cases, the network may be connected to a mesh network formed by a plurality of the sensors and the wearable devices. The wireless mesh network may employ any suitable protocol, such as Wi-Fi, Bluetooth, BLE, Bluetooth Mesh, ZigBee, body area network (BAN), IrDA, ultra wideband (UWB), etc. For example, a Wi-Fi mesh network may be used to facilitate data transfer between the plurality of sensors and wearable devices. Sensory data collected by sensors located at different places may be transferred by hopping from one sensor to another until it reaches a destination (e.g., a local control unit, a central device, user device, gateway, etc.) according to a predetermined protocol across the mesh network. In some cases, a sensor in the mesh network may comprise a communication unit such as a Wi-Fi controller responsible for deciding a data path or data link according to a routing table. The mesh network may be low power consumption. The mesh network may be robust and reliable when a sensor is added or removed from the mesh network. A configuration of the mesh network may be configured to automatically adapt to an addition or removing of a sensor of the network. In some cases, the formation of a mesh network may not require a human set up. For example, once a sensor is placed on a wall surface or indoor room of the vessel/building, the sensor module may automatically be detected and become part of the mesh network. For instance, the sensor may check its routing table and other sensors in proximity to decide a data transfer path.

The present disclosure provides a safety and risk management platform for providing adverse event prediction and detection that adapt to individuals in a remote and/or hazardous workplace. In some embodiments, one or more functionalities of the safety and risk management platform may involve using predictive models. For example, the detection of an incident (e.g., trip, slip, fall), detection of fatigue level, predicting a hazardous zone or condition may be provided using a predictive model. A predictive model may be a trained model or trained machine learning algorithm. The machine learning algorithm can be any type of machine learning network such as: a support vector machine (SVM), a naïve Bayes classification, a linear regression model, a quantile regression model, a logistic regression model, a random forest, a neural network, convolutional neural network CNN, recurrent neural network RNN, a gradient-boosted classifier or repressor, or another supervised or unsupervised machine learning algorithm (e.g., generative adversarial network (GAN), Cycle-GAN, etc.

Figure 6:
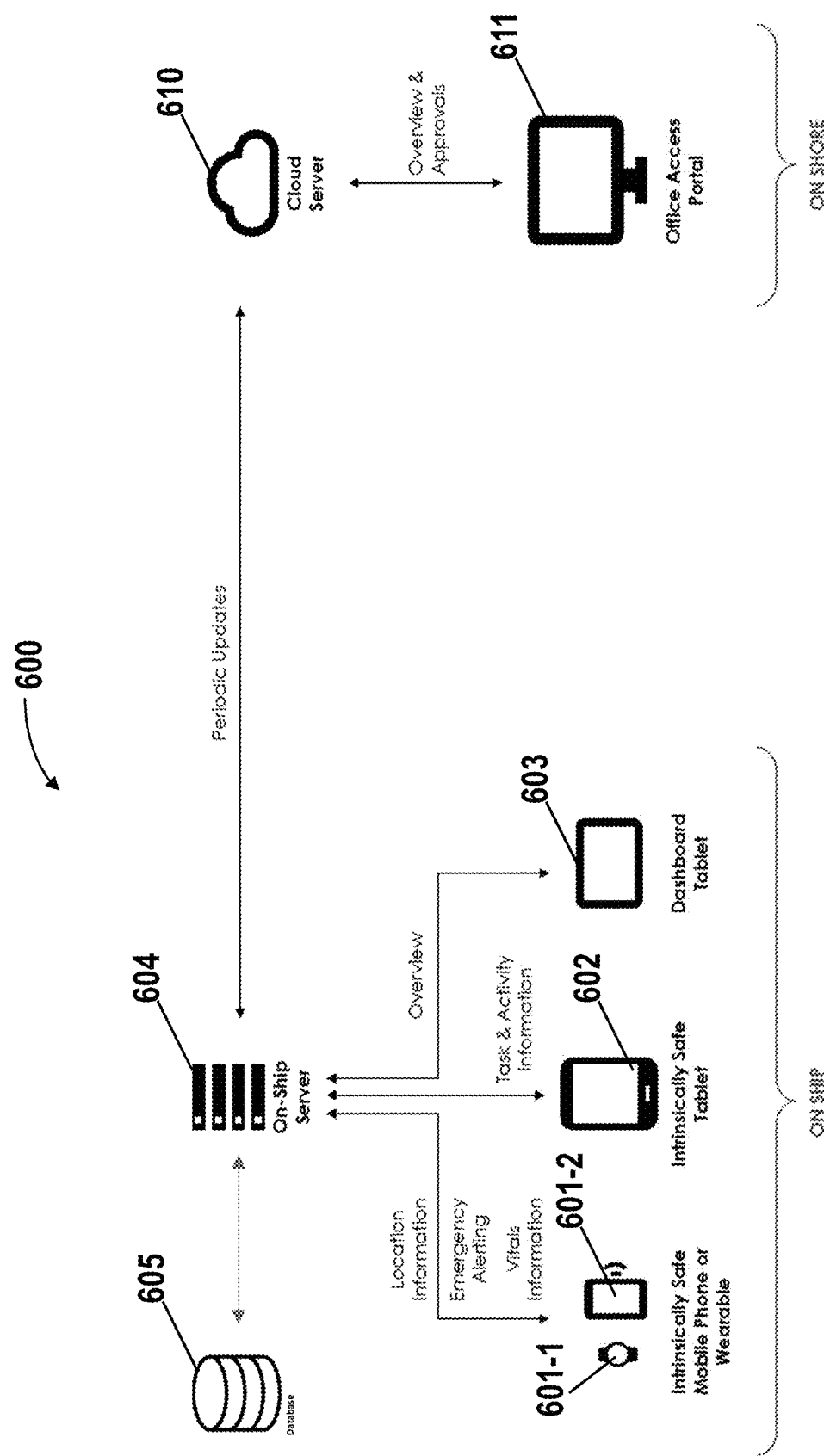
FIG. 6 schematically shows a safety and risk management system, in accordance with some embodiments of the invention.

FIG. 6 schematically shows a safety and risk management system 600, in accordance with some embodiments of the invention. As mentioned above, the safety and risk management system 600 may employ an edge intelligence paradigm that data processing and inference is performed at the edge or edge computing server 604 (e.g., on-ship server) while the predictive models may be built, developed and trained on a cloud/data center 610, and run on the edge computing server 604, user device, such as smart form tablet 602 or dashboard tablet 603 (e.g., hardware accelerator), personnel device (e.g., mobile device 601-2) and/or wearable devices 601-1 for inference.

Data collected from the personnel device (e.g., mobile device 601-2) and/or wearable devices 601-1 may comprise data captured by one or more sensors as described in FIG. 1. In some cases, data managed or transmitted from the personnel device (e.g., mobile device 601-2) and/or wearable devices 601-1 to the on-ship edge computing server 604 may include, for example, data streams from one or more sensors (e.g., location data, motion data, physiological data, etc.) and/or user input data (e.g., user initiated task request, report of an incident, alert, etc.). In some cases, data transmitted from the edge computing server 604 to the personnel device may include, for example, alert, feedback workflow instructions/guidance, or smart form generated by the edge computing server.

In some embodiments, an additional user device may be provided to an individual for managing workflow or operations. The user device may be a smart form tablet 602 or dashboard tablet 603 that is configured to display a digital smart form for safety operations management, or to view information related to operations in compliance with safety laws and real-time conditions at the worksite or related to other crewmembers. For example, personal crew data (e.g. name, rank, training credentials) may be collected via the tablet in accordance to regulatory requirements. For instance, the basic personal crew data may be required to ensure the right crew is competent to complete the safety management process. In some cases, location data and time of actions may also be captured to assure operations are in compliance with safety laws. In some cases, the provided system may be compatible with the existing safety laws or maritime laws that the captured location data and time data may be used to automatically populate a smart form for the crew to confirm and complete in accordance to laws (e.g., International Maritime Organization guidelines). The provided safety and risk management system may also allow for personalized or customized procedural forms set up by an organization (e.g., crew ship company) to ensure safety of crew.

The user device (e.g., a smart form tablet 602 or dashboard tablet 603) may be in communication with the edge computing server 604. Data transmitted from the user device 602, 603 to the edge computing server 604 may include, for example, the basic personal crew data and user inputted data in the digital smart form (e.g., confirmation of a task is completed), report provided by the crewmember and the like. Data transmitted from the edge computing server to the user device may include, for example, digital form to be filled, alert, real-time information about a hazardous situation on the vessel and the like. It is noted that in some cases, some of the above-mentioned functionalities can also be performed by the personnel device such as the mobile device 601-2. Similarly, some of the functionalities such as location tracking and motion tracking performed by the personnel devices (e.g., wearable device) may be performed by the user device.

The edge computing server 604 may analyze the data stream with aid of one or more predictive models, the output result may be an alert indicating a detected incident such as fall or trip, a prediction of a impeding adverse event such as a hazardous condition in a work zone, and various other functionalities as described elsewhere herein. The edge computing server 604 may be coupled to a local database 605.

The local database 605 may comprise storage containing a variety of data consistent with disclosed embodiments. For example, the databases may store, for example, raw data collected from the user device, sensors and wearable device, each individual's historical data, data about a predictive model (e.g., parameters, hyper-parameters, model architecture, training dataset, performance metrics, threshold, rules, etc), data generated by a predictive model (e.g., intermediary results, output of a model, latent features, input and output of a component of the model system, etc.), incident report, record, smart form, workflow, safety law or regulatory related data, and user provided information (e.g., confirmation or denial of a prediction result, user information such as name, credential, confirmation of completing a task at different time points, etc), predictive models, algorithms, and the like. In certain embodiments, one or more of the databases may be co-located with the edge computing server, may be co-located with one another on the local network, or may be located separately from other local devices. One of ordinary skill will recognize that the disclosed embodiments are not limited to the configuration and/or arrangement of the database(s).

The local database 605 may be one or more memory devices configured to store data. Additionally, the databases may also, in some embodiments, be implemented as a computer system with a storage device. In one aspect, the databases may be used by components of the network layout to perform one or more operations consistent with the disclosed embodiments. One or more cloud databases of the platform may utilize any suitable database techniques. For instance, structured query language (SQL) or "NoSQL" database may be utilized for storing the data transmitted from the edge computing system or the local network such as real-time data (e.g., location data, motion data, audio/video data, messages, etc), processed data such as report, alert, historical data, predictive model or algorithms. Some of the databases may be implemented using various standard data-structures, such as an array, hash, (linked) list, struct, structured text file (e.g., XML), table, JavaScript Object Notation (JSON), NOSQL and/or the like. Such data-structures may be stored in memory and/or in (structured) files. In another alternative, an object-oriented database may be used. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. In some embodiments, the database may include a graph database that uses graph structures for semantic queries with nodes, edges and properties to represent and store data. If the database of the present invention is implemented as a data-structure, the use of the database of the present invention may be integrated into another component such as the component of the present invention. Also, the database may be implemented as a mix of data structures, objects, and relational structures. Databases may be consolidated and/or distributed in variations through standard data processing techniques. Portions of databases, e.g., tables, may be exported and/or imported and thus decentralized and/or integrated.

In some cases, batch data, and/or individual records, report and the like may be generated by the edge computing server. Some of the data may be stored in the local database 604, while some of the data may be transmitted to a remote cloud 610.

The remote cloud 610 may comprise one or more cloud applications such as a management console or cloud analytics portal that can be accessed by onshore superintendents, fleet managers, fleet directors, shipowners, managers, auditors or third-party entities. For example, an office access portal 611 may be provided by the remote cloud and can be accessed by onshore users such as a superintendent. The third-party entity may access the cloud data repository or cloud applications for various purposes such as customer/oil major vetting, customer/oil major administered tanker management self-assessment, P&I Club inspection, class certification, internal auditors, port state control inspection or flag state inspection.

In one aspect, the present disclosure provides an integrated platform for controlling work flow, detecting, predicting and managing risks in a workplace such as marine industry. The integrated platform may be a safety and risk management platform that may help vessel operators to comply with safety laws and regulation or maritime regulations and laws, improve crew situational awareness for hazardous work, enforce pro-active safety behaviors based on real-time tracking and situation detection, and provide a single access-point for all audit and survey documents and data. The safety and risk management platform may provide various functionalities including, for example, automating a workflow, providing a digital, smart form, detecting an adverse event (e.g., fall or trip detection), predicting and forecasting hazardous condition in a work zone, enforcing behavior change to comply with safety laws and the like. In some cases, at least some of the above-mentioned functionalities may employ machine learning techniques.

In some embodiments, the safety and risk management platform may be capable of performing adverse event prediction and detection that adapt to individuals in a remote and/or hazardous workplace. In some embodiments, one or more functionalities of the safety and risk management platform may involve using predictive models. For example, the detection of an incident (e.g., trip, slip, fall), detection of a fatigue level, predicting or forecasting a hazardous condition in a work zone may be provided using a predictive model. A predictive model may be a trained model or trained machine learning algorithm. The machine learning algorithm can be any type of machine learning network such as: a support vector machine (SVM), a naïve Bayes classification, a linear regression model, a quantile regression model, a logistic regression model, a random forest, a neural network, convolutional neural network CNN, recurrent neural network RNN, a gradient-boosted classifier or repressor, or another supervised or unsupervised machine learning algorithm (e.g., generative adversarial network (GAN), Cycle-GAN, etc.

In some cases, the safety and risk management platform may provide predictive models with continual training or improvement after deployment. The predictive model provided by the platform may be dynamically adjusted and tuned to adapt to different individuals, different vessels, or different fleets over time. The predictive model provided by the platform may be improved continuously over time (e.g., during implementation, after deployment). Such continual training and improvement may be performed automatically with little user input or user intervention. The safety and risk management platform may also allow onboard supervisors and users, or remote entities such as onshore managers to monitor adverse event occurrence. The backend predictive model system can be applied in various scenarios such as in cloud or an on-premises environment.

Figure 7:
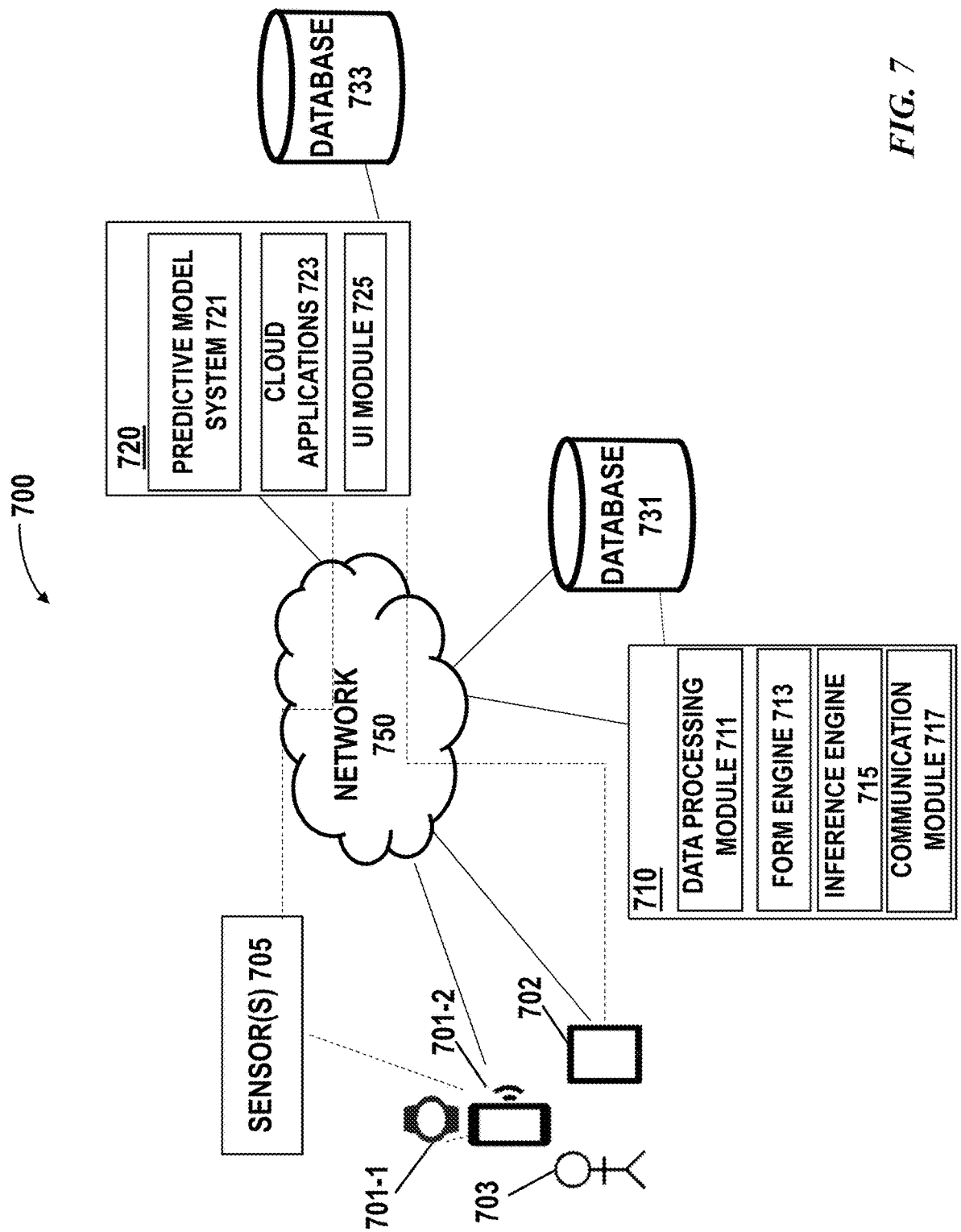
FIG. 7 schematically shows an example of a safety and risk management platform, in accordance with some embodiments of the invention.

FIG. 7 schematically shows an example of a safety and risk management platform 700, in accordance with some embodiments of the invention. The safety and risk management platform 700 may include one or more personnel device or sensor devices 701-1, 701-2, an edge computing system 710, a remote entity (e.g., a cloud) 720, and a database 733, 731. The safety and risk management platform 700 may optionally comprise one or more user devices 702 (e.g., smart tablet) that can be the same as the user devices (e.g., smart form tablet 602 or dashboard tablet 603) as described in FIG. 6. Each of the components 701-1, 701-2, 710, 720, 733, 731 may be operatively connected to one another via network 750 or any type of communication links that allows transmission of data from one component to another. The platform may employ an edge intelligence paradigm and the network 750 may have configurations as described elsewhere herein.

One or more components of the safety and risk management platform 700 may reside on the remote entity 720 (e.g., a cloud). The remote entity 720 may be a data center, a cloud, a server, and the like that is in communication with one or more components local to the worksite. For example, the remote entity may be in communication with the edge computing system, or sensor devices onboard a vessel. In some cases, the remote entity can be the same as the cloud server as described in FIG. 6. For example, the remote entity may be in communication with the on-ship edge computing system via a gateway that data may be transmitted from the vessel to the cloud at a lower frequency due to the remote geo-location of the vessel.

In some cases, the remote entity (e.g., cloud) 720 may include services or applications that run in the cloud or an on-premises environment to remotely configure and manage the edge computing system over the network 750. In some embodiments, the remote entity may host a plurality of functional components such as a predictive model system 721, one or more cloud applications 723, a user interface module 725 or other components.

In some cases, the cloud applications 723 may process or analyze data transmitted from the local worksite (e.g., vessel) for various use cases. The cloud applications may, for example, allow for a range of use cases such as customer/oil major vetting, customer/oil major administered tanker management self-assessment, P&I Club inspection, class certification, internal auditors, port state control inspection or flag state inspection.

In some embodiments, the cloud applications 723 may also comprise a management console or cloud analytics portal that can be accessed by onshore superintendents, fleet managers, fleet directors, shipowners, auditors, managers or third-party entities. For example, an office access portal may be provided by the cloud analytics portal and can be accessed by onshore users such as a superintendent.

In some embodiments, the remote entity may host or comprise a predictive model system 721. In some cases, the predictive model system may comprise a model creator and a model manager. In some cases, a model creator may be configured to train, develop or test a predictive model using data from a cloud data lake (e.g., database 733) and/or metadata database that stores contextual data (e.g., deployment context). The model manager may be configured to manage data flows among the various components (e.g., cloud data lake, metadata database, local database 731, edge computing system, model creator), provide precise, complex and fast queries (e.g., model query, metadata query), model deployment, maintenance, monitoring, model update, model versioning, model sharing, and various others. For example, the deployment context may be different depending on edge infrastructure (e.g., types of workplace, volume/are of worksite, applications onboard the edge infrastructure, fleet information, etc.) and the model manager may take into account the application manifest such as edge hardware specifications, deployment location, information about compatible systems, data-access manifest for security and privacy, emulators for modeling data fields unavailable in a given deployment and version management during model deployment and maintenance.

The edge intelligence paradigm may allow for data processing and inference performed at the edge or edge computing system 710 while the predictive models may be built, developed and trained on a cloud/data center 720, and run on the edge computing system 710, user device such as smart form tablet or dashboard tablet 702 (e.g., hardware accelerator), personnel devices (e.g., mobile device 701-2) and/or wearable devices 701-1 for inference. For instance, sensor data stream may be sent to the on-ship edge computing system 710 in real-time for detecting incident (e.g., trip, slip or fall), predicting and forecasting hazardous situations (e.g., identifying hazardous work zone or environmental conditions, etc.), identifying individual's physiological condition (e.g., fatigue, health condition, etc.), managing on-ship operations, safety and risk (e.g., while the vessel is in motion), whereas a message package comprising batch data may be sent to a fleet manager or cloud 720 (e.g., while the vessel or cruise ship returns to the port or seashore) at a lower frequency.

In some cases, the predictive model for detecting an adverse event or predicting hazardous condition may be pre-trained on the cloud and transmitted to the user device, wearable device or edge computing system for implementation. In some cases, the predictive model may go through continual training as new sensor data and user feedback are collected. The continual training may be performed on the cloud or on the server 720. In some cases, sensor data may be transmitted to the cloud 720 which are used to update the model for continual training and the updated model (e.g., parameters of the model that are updated) may be downloaded to the local or edge system (e.g., user device, software application of the on-ship system) for implementation.

In some cases, the cloud or data center 720 may further comprise a user interface (UI) module 725 for viewing analytics, reports, sensor data (e.g., image), and/or processed data. In some cases, the UI may also include a management UI for developing and deploying analytics expressions, deploying trained predictive models to the edge (e.g., vessel operating system, edge gateway, edge infrastructure, wearable device, user device, form engine, inference engine, etc.) for inference, or configuring and monitoring the edge computing system.

In some cases, the graphical user interface (GUI) or user interface provided by the UI module 725 may be provided on a display. The display may or may not be a touchscreen. The display may be a light-emitting diode (LED) screen, organic light-emitting diode (OLED) screen, liquid crystal display (LCD) screen, plasma screen, or any other type of screen. The display may be configured to show a user interface (UI) or a graphical user interface (GUI) rendered through a mobile application or cloud application (e.g., via an application programming interface (API) executed on the onshore manager's user device). Similarly, a GUI may also be provided by the edge computing system 710 and the GUI may be provided on a display of the wearable device, personnel device, user device at the worksite. The GUI may be rendered through an application (e.g., via an application programming interface (API) executed on the wearable device, personnel device, user device, local supervisor's user device, etc.)

In some cases, the cloud or data center 720 may include applications that allow for integrated administration and management, including monitoring or storing of data in the cloud database 733 or at a private data center.

The cloud database 733 may be one or more memory devices configured to store data. Additionally, the databases may also, in some embodiments, be implemented as a computer system with a storage device. In one aspect, the databases may be used by components of the network layout to perform one or more operations consistent with the disclosed embodiments. One or more cloud databases of the platform may utilize any suitable database techniques. For instance, structured query language (SQL) or "NoSQL" database may be utilized for storing the data transmitted from the edge computing system or the local network such as real-time data (e.g., location data, motion data, audio/video data, messages, etc), processed data such as report, alert, historical data, safety law or regulatory related data, predictive model or algorithms. Some of the databases may be implemented using various standard data-structures, such as an array, hash, (linked) list, struct, structured text file (e.g., XML), table, JavaScript Object Notation (JSON), NOSQL and/or the like. Such data-structures may be stored in memory and/or in (structured) files. In another alternative, an object-oriented database may be used. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. In some embodiments, the database may include a graph database that uses graph structures for semantic queries with nodes, edges and properties to represent and store data. If the database of the present invention is implemented as a data-structure, the use of the database of the present invention may be integrated into another component such as the component of the present invention. Also, the database may be implemented as a mix of data structures, objects, and relational structures. Databases may be consolidated and/or distributed in variations through standard data processing techniques. Portions of databases, e.g., tables, may be exported and/or imported and thus decentralized and/or integrated.

The cloud database 733 may comprise storage containing a variety of data consistent with disclosed embodiments. For instance, the databases may store, for example, selected real-time data transmitted form the local network (e.g., data collected from the user device, sensors and wearable device), each individual's historical data, data about a predictive model (e.g., parameters, hyper-parameters, model architecture, training dataset, performance metrics, threshold, rules, etc), data generated by a predictive model (e.g., intermediary results, output of a model, latent features, input and output of a component of the model system, etc.), incident report, record and user provided information (e.g., confirmation or denial of a prediction result, user information such as name, credential, etc), safety law related data, smart forms, predictive models, algorithms, and the like. In certain embodiments, one or more of the databases may be co-located with the server 720, may be co-located with one another on the network, or may be located separately from other devices. One of ordinary skill will recognize that the disclosed embodiments are not limited to the configuration and/or arrangement of the database(s).

In some embodiments, the platform 700 may construct the database 733 for fast and efficient data retrieval, query and delivery. For example, the cloud 720 may provide customized algorithms to extract, transform, and load (ETL) the data. In some embodiments, the management console residing on the cloud may construct the databases using proprietary database architecture or data structures to provide an efficient database model that is adapted to large scale databases, is easily scalable, is efficient in query and data retrieval, or has reduced memory requirements in comparison to using other data structures.

In some embodiments, the edge computing system 710 may be an edge intelligence platform. For example, the edge computing system 710 may be a software-based solution based on fog or edge computing concepts which extend data processing and inference closer to the edge (e.g., onboard vessel). While edge computing may refer to the location where services are instantiated, fog computing may imply distribution of the communication, computation, and storage resources and services on or in proximity to (e.g., within 5 meters or within 1 meter) devices and systems in the control of end-users or end nodes. Maintaining close proximity to the edge devices (e.g., edge computing server, sensors, user devices, personnel devices, etc.) rather than sending all data to a distant centralized cloud, minimizes latency allowing for maximum performance, faster response times, and more effective maintenance and operational strategies. It also significantly reduces overall bandwidth requirements and the cost of managing widely distributed networks.

The edge computing system 710 onboard the vessel and/or the remote entity 720 may employ any suitable technologies such as container and/or micro-service. For example, the application of the edge computing system (e.g., smart form engine, inference engine, etc.) can be a containerized application. The edge computing system may deploy a micro-service based architecture in the software infrastructure at the edge such as implementing an application or service in a container. In another example, the cloud applications and/or the predictive model system may provide a management console or cloud analytics backed by microservices.

In some embodiments, the edge computing system 710 may comprise a plurality of components including a data processing module 711, a form engine 713, an inference engine 715, and a communication module 717.

In some cases, at least a portion of data processing can be performed at the edge (i.e., user device, personnel device, wearable device or the edge computing server). The data processing module 711 may provide pre-processing of stream data and batch data collected from the sensor devices 701-1, 701-2, user devices 702 and other devices connected to the local network onboard the vessel. In some embodiments, the data processing module 711 may support ingesting of sensor data into a local storage repository 731 (e.g., local time-series database), data cleansing, data enrichment (e.g., decorating data with metadata), data alignment, data annotation, data tagging, data aggregation, and various other data processing. Data from the user devices (e.g., dashboard tablet, digital form tablet, etc.), sensors, wearable device 701-1, mobile device 701-2 and various other sources as described elsewhere herein may be ingested and processed by the data processing module. For instance, the data processing module may collect or ingest data from the sensors via one or more protocols (e.g., MQ Telemetry Transport, OPC Unified Architecture, Modbus, and DDS). The data provided or outputted by the sensors may be a binary data stream. The transmission or delivery of this data from the sensors to the data processing module can be push or pull methods. In some cases, the data processing module may enrich the incoming data from the sensors by decoding the raw binary data into consumable data formats (such as JavaScript Object Notation) and also decorating with additional necessary and useful metadata.

In some cases, the data processing module 711 may be configured to preprocess continuous streams of raw data or batch data transmitted from the local network and prepare the data to be processed by the inference engine. For instance, data may be processed so it can be fed into machine learning analyses. Data processing may include, for example, data normalization, labeling data with metadata, tagging, data alignment, data segmentation, and various others. In some cases, the processing methodology may be programmable through APIs by the developers constructing the machine learning analysis via the cloud applications or the UI portal 725.

The data processing module 711 may process the real-time data collected at the edge device or local devices before sending to the cloud. In some cases, at least a portion of the pre-processed data may be transmitted to the cloud for training or updating a model. In some cases, the data processing module 711 may be coupled to the communication module 717 to prepare the data for transmission based on a transmission scheme. For example, the data processing module 711 may also be configured to aggregate the raw data across a time duration (e.g., about 1, 2, 3, 4, 5, 6, 7, 8, 9, 10 seconds, about 1, 2, 3, 4, 5, 6, 7, 8, 9, 10 minutes, about 1, 2, 3, 4, 5, 6, 7, 8, 9, 10 hours, etc.), across data types (e.g., accelerometer data, physiological data, location data, audio data, video data, user input, image data, etc.) or different sources, and send the aggregated data to a remote entity 720 (e.g., cloud) as a package.

The form engine 713 may be configured to provide a digital form compatible with the existing safety laws or maritime laws. The form engine may automatically generate a smart form based on real-time location data and time data form for the crew to confirm and complete in accordance with laws (e.g., International Maritime Organization guidelines). The smart form may be provided with additional layers of authentication and assurance and can be used to manage workflows in a step-by-step manner. For example, based on the location data and time data, the amount of time each individual has spent on the assigned task may be tracked. Such data may be used to verify that work has been done within time in compliance with the workflow. In some cases, the form generated by the form engine may be an incident report form. For example, upon detection an incident or a user input request, a form may be automatically filled the crew members' name, date, time, location, and type of incident that occurred.

In some cases, the form engine may perform workflow generation or the incident form auto-fill functionality using a predictive model. The example, the form engine may process real-time sensor data such as location data and/or user input data using a trained predictive model and the output may be a next step/operation to be performed by the individual or an incident form with predicted incident. As described above, the trained predictive model may be trained, developed and built on the cloud and is downloaded to the edge computer system for inference. Details about the smart form are described later herein.

The inference engine 715 may process real-time data captured by the user devices (e.g., dashboard tablet, digital form tablet, etc.), sensors, wearable device 701-1, mobile device 701-2 using one or more predictive models. Similarly, the one or more predictive models can be downloaded from the cloud. The inference engine 715 may perform various functions such as generating preventive procedural alerts and warnings, generating a streamlined safety workflow or operation processes, detecting crew-based metrics (e.g., fatigue level, health condition, under-stress, physiological state, etc.), detecting an incident (e.g., trip, slip or fall detection), predicting an impeding adverse event (e.g., hazardous condition forecasting, identifying a hazardous situation or conditions in a work zone, etc.), and identifying an efficient workflow or tasks assignment for one or more operators and one or more groups. Details about the various functions are described later herein.

The communication module 717 may be configured to determine which of the local data or which portion of the local data stays in the local database 731, is to be moved/transmitted to the cloud database 733. The communication module may also determine which of the local data or which portion of the local data is to be communicated to which data center, a cloud database or third party entity, when and at what frequency this portion of data is transmitted. In some cases, data that is off-loaded or moved to the cloud database may be deleted from the local database for improved storage efficiency. Alternatively, data in the local database may be preserved for a pre-determined period of time after it is off-loaded to the cloud database.

In some embodiments, data may be transmitted from the edge computing system or local database to the cloud according to a transmission scheme. In some cases, the transmission scheme may specify which of the local data or which portion of the local data stays in the local database 731, is to be moved/transmitted to the cloud database 733. The transmission scheme may also specify which of the local data or which portion of the local data is to be communicated to which data center, a cloud database or third party entity, when and at what frequency this portion of data is transmitted. For example, a data transmission scheme may comprise timing of transmission such as delay time or frequency, communication protocol, compression or encryption method used for transmission, and various others (e.g., regulatory rules regarding privacy before data is transmitted).

In some cases, the data transmission scheme may also specify how data are transmitted. For instance, the data transmission scheme may specify compression methods (e.g., lossless compression algorithm, lossy compression algorithms, encoding, etc), or encryption methods (e.g., RSA, triple DES, Blowfish, Twofish, AES, etc) used for transmission. In some cases, a data compression method and/or encryption method may be determined for a transmission based on rules. For example, a rule may determine the compression method and/or encryption method according to a given type of data, the application that uses the data, destination of the data and the like. The rules for determining data compression method and/or encryption method may be stored in a local database, such as the local database 731, accessible to the communication module 717 or the edge computing system 710. In some cases, the rule for determining the data compression method and/or encryption method may be part of the rule for determining the data transmission. For instance, a ruleset for determining the encryption method or compression method may be called (e.g., by ruleset identifier) for determining the data transmission scheme.

The data transmission scheme may be determined based on a set of rules. The set of rules may be handcrafted rules. For example, pre-determined or hand-crated rules about compression method and/or encryption method may be applied upon receiving a transmission request specifying the type of data, data related to an application, destination of data, and the like. Such hand-crafted rules may be stored in a local database accessible to the communication module 717 or the edge computing system 710. For instance, at least a portion of the local data may be transmitted to a remote entity (e.g., cloud applications) according to a pre-determined data transmission scheme that is not generated using machine learning algorithms. For instance, in some situations, when the data transmission is infrequent or the amount of data to be transmitted is relatively small, a data transmission scheme may be generated based on a request from a cloud application or based on a geolocation of the gateway or the edge device.

In some cases, the compression method and/or encryption method may be determined by machine learning algorithm trained models. For instance, a trained model may be applied to the set of data to be transmitted and generate a rule for compressing or encrypting the set of data. In other instances, the trained model may determine a data transmission scheme based on a detected geo-location of the gateway and the destination.

The local database 731 can be the same as the local database as described in FIG. 6. For example, the local database 731 may comprise storage containing a variety of data consistent with disclosed embodiments. For example, the databases may store, for example, raw data collected from the user device, sensors and wearable device, each individual's historical data, data about a predictive model (e.g., parameters, hyper-parameters, model architecture, training dataset, performance metrics, threshold, rules, etc), data generated by a predictive model (e.g., intermediary results, output of a model, latent features, input and output of a component of the model system, etc.), incident report, record, smart form, workflow, safety law or regulatory related data, and user provided information (e.g., confirmation or denial of a prediction result, user information such as name, credential, confirmation of completing a task at different time points, etc), predictive models, algorithms, and the like. In certain embodiments, one or more of the databases may be co-located with the edge computing server, may be co-located with one another on the local network, or may be located separately from other local devices. One of ordinary skill will recognize that the disclosed embodiments are not limited to the configuration and/or arrangement of the database(s).

In some embodiments, the edge computing system 710 may construct the local database 731 for fast and efficient data retrieval, query and delivery. For example, the edge computing system may provide customized algorithms to extract, transform, and load (ETL) the data. In some embodiments, the edge computing system may construct the databases using proprietary database architecture or data structures to provide an efficient database model that is adapted to large scale databases, is easily scalable, is efficient in query and data retrieval, or has reduced memory requirements in comparison to using other data structures.

The edge computing system 710 may analyze input data (e.g., sensor data) from the personnel device 701-1, 701-2, sensor(s) 705, wearable device 701-1, user device 702 in order to generate safety and risk related results (e.g., predict and detect an adverse event, generate an optimal task assignment) and to provide feedback information (e.g., alert, stimulation cues, warning, guidance, etc.). The edge computing system may be configured to perform one or more operations consistent with the disclosed methods described later and elsewhere herein. In some embodiments, one or more of the functionalities may be implemented on the edge computing server. In other embodiments, one or more of the functionalities may be implemented on the user device. Additionally, a portion of the one or more of the functionalities may be implemented on the sensor(s), personnel device or wearable device. The one or more of the functionalities may be implemented using software, hardware, or a combination of software and hardware in one or more of the above-mentioned components within the platform.

The personnel device 701-1, 701-2 may comprise one or more sensors 705. The one or more sensors 705 may be on-board the personnel device or operably coupled to the personnel device. In some alternative embodiments, the one or more sensors 705 may be located external to the user device, and sensory data may be transmitted to the user device via communication approaches described elsewhere herein. The one or more sensor (e.g., physiologic sensor, kinematic sensor, motion sensor, audio sensor, field sensor, etc.) can be controlled by an application/software configured to collect sensory data about the user or the ambient environment.

As described above, the one or more sensors may comprise various types of sensors such as physiologic sensors, kinematic sensors, audio sensors and the like. Examples of types of sensors may include inertial sensors (e.g., accelerometers, magnetometers, gyroscopes, and/or gravity detection sensors, which may form inertial measurement units (IMUs)), location sensors (e.g., global positioning system (GPS) sensors, mobile device transmitters enabling location triangulation), heart rate monitors, external temperature sensors, skin temperature sensors, skin conductance, neural signals (e.g. EEG), muscle signals (e.g. EMG), capacitive touch sensors, sensors configured to detect a galvanic skin response (GSR), vision sensors (e.g., imaging devices capable of detecting visible, infrared, or ultraviolet light, such as cameras), proximity or range sensors (e.g., ultrasonic sensors, lidar, time-of-flight or depth cameras), altitude sensors, attitude sensors (e.g., compasses), pressure sensors (e.g., barometers), humidity sensors, vibration sensors, audio sensors (e.g., microphones), and/or field sensors (e.g., magnetometers, electromagnetic sensors, radio sensors). In some cases, the user device or the sensors may be capable of delivering an alert (e.g., vibration, audio alarm, etc.) in response to a detection of an incident (e.g., trip, fall) or forecasting a hazardous situation (e.g., prediction of a dangerous event in the environment or a physiological condition of the individual). For example, upon the prediction of an impending adverse event (e.g., entering a hazarders zone, reaching a fatigue level), intervention such as rhythmic cue, audio, visual, or tactile stimulus may be delivered to the crewmember via the user device or sensors.

In some cases, the safety and risk management platform may comprise sensors deployed in various locations onboard the vessel for detecting a hazardous situation or adverse event in the environment or at the worksite. Such sensors can include, for example, the navigation system, sensors onboard the vessel such as laser imaging detection and ranging (Lidar), radar, sonar, differential global positioning system (DGPS), inertial measurement unit (IMU), gyroscopes, magnetometers, accelerometers, ultrasonic sensors, image sensors (e.g., visible light, infrared), heat sensors, audio sensors, vibration sensors, conductivity sensors, chemical sensors, biological sensors, radiation sensors, conductivity sensors, proximity sensors, or any other type of sensors, or combination thereof. The one or more sensors deployed on the vessel may work in conjunction with the sensor or user devices for location and time-based tracking (e.g., proximity sensor, Beacon, etc), incident detection (e.g., temperature, chemical leakage, etc), and providing situational awareness to the individuals.

In optional embodiments, user device 702 may be provided for displaying a workflow or enforcing safety operations. The user device 702 and the personnel devices may be a computing device configured to perform one or more operations consistent with the disclosed embodiments. Examples of user devices and personnel devices may include, but are not limited to, mobile devices, smartphones/cellphones, tablets, personal digital assistants (PDAs), laptop or notebook computers, desktop computers, virtual reality systems, augmented reality systems, microphones, or any electronic device capable of analyzing, receiving ((e.g., receiving user input for continued learning process), providing or displaying certain types of feedback data (e.g., adverse event analysis, prediction result, etc.) to a user. The user device or personnel device may be any electronic device capable of analyzing, receiving user input data (e.g., receiving user input for incident report, fill-in a smart form), providing or displaying certain types of feedback data (e.g., adverse event statistics, alert, etc.) to a user.

The user device or personnel devices may be a handheld object. The user device or personnel devices may be portable. The user device or personnel devices may be carried by a human user. In some cases, the user device may be located remotely from a human user, and the user can control the user device using wireless and/or wired communications.

User device or personnel devices may include one or more processors that are capable of executing non-transitory computer readable media that may provide instructions for one or more operations consistent with the disclosed embodiments. The user device may include one or more memory storage devices comprising non-transitory computer readable media including code, logic, or instructions for performing the one or more operations. The user device may include software applications that allow the user device to communicate with and transfer data between sensor(s) sensor(s) 705, wearable device 701-1, edge computing server 710, the cloud 720, and/or database 731, 733. The user device or personnel devices may include a communication unit, which may permit the communications with one or more other components in the platform 700. In some instances, the communication unit may include a single communication module, or multiple communication modules. In some instances, the user device or personnel devices may be capable of interacting with one or more components in the platform 700 using a single communication link or multiple different types of communication links in consistent with the network configuration and architecture as described elsewhere herein.

User device 702 and personnel device 701-1, 701-2 may include a display. The display may be a screen. The display may or may not be a touchscreen. The display may be a light-emitting diode (LED) screen, OLED screen, liquid crystal display (LCD) screen, plasma screen, or any other type of screen. The display may be configured to show a user interface (UI) or a graphical user interface (GUI) rendered through an application (e.g., via an application programming interface (API) executed on the user device). The GUI may show prediction result, alert, visual stimulations upon a prediction/detection, and images, charts, interactive elements relating to the workflow process, live conditions on the vessel, and real-time prediction and detection result. The GUI may permit a user to input user feedback (e.g., confirm completion of a task, input an incident report, etc.). One or more of the applications, user interfaces (e.g., dashboard, safety portal, etc.) may be hosted by the edge computing server and/or run on the user device 702 and personnel device 701-1, 701-2.

In some cases, third-party user interfaces or software applications may be integrated to the client application and integrated in the front-end user interface (e.g., within the GUI). The third-party user interfaces, resource or data may be, for example, standard IMO regulated forms or safety law related interface. In some cases, third-party resources in compliance with safety or maritime laws may be used to provide a workflow in compliance with the law or rules. In some cases, the GUI may permit an individual (e.g., crewmember) to submit a report to the platform with simple user operation (e.g., one-click button or voice command) in response to a detection or prediction of an adverse event. For instance, an individual may tap a button on the GUI then a report or message is automatically generated and sent to the edge computing server with the current location of the user device or personnel device. Alternatively or in addition, a text message may be sent from the user device, wearable device or personnel device to the edge computing server where the text message may comprise the current location of the individual or a brief description of the adverse event (e.g., trip, fall, fatigue, in a hazardous zone, etc.) automatically generated by the system.

In some embodiments, an alert or notification about an adverse event prediction or detection may be generated and delivered in real-time without user interference. Such alert or notification may be delivered to the individual, other members on the vessel, and a manager via any suitable approach or be in any suitable form, such as audio, visual, or tactile feedback. In some cases, a feedback may be delivered to the individual to change a behavior of the individual or warn the individual regarding a impeding adverse event. The feedback may be delivered through the user device 702, the sensor(s) 705, the wearable device 701-1, or any device that is capable of presenting one or more stimulations, such as visual stimulations, audio stimulations, and/or haptic stimulations. For example, a rhythmic tactile stimulation may be delivered to the individual via a wireless actuator worn by the individual or via the mobile device. The alert or notification may be delivered to other individuals at the worksite or in the workplace (e.g., manager, other crewmembers) in any suitable forms (e.g., audio, visual alert in a GUI) via the local network.

In some embodiments, a user 703 (e.g., crewmember, operator) may be associated with one or more sensors 705, or one or more wearable devices 701-1. The one or more wearable devices may also comprise sensors that collect sensory data to be processed by the edge computing system. Any description herein relating to sensor(s) 705 can also be applied to sensors on-board the personnel device or user device, and wearable device 701-1. In some cases, the sensors 705 and/or the wearable device may be capable of delivering a feedback (e.g., electrical stimulus, audio alarm, etc.) to the individual 703 in response to a detection or prediction result. The one or more sensors may comprise various types of sensors such as physiologic sensors, kinematic sensors, and the like. Examples of types of sensors may include inertial sensors (e.g., accelerometers, gyroscopes, and/or gravity detection sensors, which may form inertial measurement units (IMUs)), location sensors (e.g., global positioning system (GPS) sensors, mobile device transmitters enabling location triangulation), heart rate monitors, external temperature sensors, skin temperature sensors, skin conductance, neural signals (e.g. EEG), muscle signals (e.g. EMG), capacitive touch sensors, sensors configured to detect a galvanic skin response (GSR), vision sensors (e.g., imaging devices capable of detecting visible, infrared, or ultraviolet light, such as cameras), proximity or range sensors (e.g., ultrasonic sensors, lidar, time-of-flight or depth cameras), altitude sensors, attitude sensors (e.g., compasses), pressure sensors (e.g., barometers), humidity sensors, vibration sensors, audio sensors (e.g., microphones), and/or field sensors (e.g., magnetometers, electromagnetic sensors, radio sensors).

The one or more sensors 705 may be located on the individual's body (e.g., attached to skin), a part of body (e.g., wearable device 701-1) or clothing. The one or more sensors may be in communication with sensor located remotely from an individual, such as deployed in an environment (e.g. Beacon device). The one or more sensors 705 or the wearable device 701-1 may be operatively coupled to the user device 702, personnel device 701-2 or one another, such as via wired or wireless (e.g., Bluetooth, Wi-Fi, Near Field Communication (NFC), etc.) connections. The one or more sensors 705 or the wearable device 701-1 may be in communication with the edge computing system or the cloud, such as via the network 750. The wearable device 701-1 may be, for example, smartwatches, wristbands, glasses, gloves, headgear (such as hats, helmets, virtual reality headsets, augmented reality headsets, head-mounted devices (HMD), headbands), pendants, armbands, leg bands, shoes, vests, motion sensing devices, etc.

The edge computing system 710 may be implemented in software, hardware or a combination of both. In some cases, the edge computing system 710 may be implemented by one or more processors. For example, the edge computing system 710 may be implemented by an edge computing server which can be one or more server computers configured to perform one or more operations consistent with the disclosed embodiments. In one aspect, the server may be implemented as a single computer, through which user device, wearable device or sensors are able to communicate with the edge computing system and database. In some embodiments, the user device, wearable device or sensors communicate with the edge computing system directly through the local network. In some embodiments, the server may embody the functionality of one or more of the edge computing system. A server may include known computing components, such as one or more processors, one or more memory devices storing software instructions executed by the processor(s), and data. A server can have one or more processors and at least one memory for storing program instructions. The processor(s) can be a single or multiple microprocessors, field programmable gate arrays (FPGAs), or digital signal processors (DSPs) capable of executing particular sets of instructions. Computer-readable instructions can be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the methods can be implemented in hardware components or combinations of hardware and software such as, for example, ASICs, special purpose computers, or general purpose computers.

The various functions performed supported by the edge or edge device such as data processing, making inference using a trained model and the like may be implemented in software, hardware, firmware, embedded hardware, standalone hardware, application specific-hardware, or any combination of these. The edge computing system, edge computing server, and techniques described herein may be realized in digital electronic circuitry, integrated circuitry, specially designed ASICs (application specific integrated circuits), computer hardware, firmware, software, and/or combinations thereof. These systems, devices, and techniques may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. These computer programs (also known as programs, software, software applications, or code) may include machine instructions for a programmable processor, and may be implemented in a high-level procedural and/or object-oriented programming language, and/or in assembly/machine language. As used herein, the terms "machine-readable medium" and "computer-readable medium" refer to any computer program product, apparatus, and/or device (such as magnetic discs, optical disks, memory, or Programmable Logic Devices (PLDs)) used to provide machine instructions and/or data to a programmable processor.

Network 750 may be a network that is configured to provide communication between the various components illustrated in FIG. 7. The network may be implemented, in some embodiments, as one or more networks that connect devices and/or components in the network layout for allowing communication between them. For example, user device 702, sensor(s) 705, wearable device 701-1, personnel device 701-2, edge computing system 710, cloud 720 and database 731, 733 may be in operable communication with one another over network 750. In some embodiments, the network may employ a configuration and layout as described in FIGS. 2-5. Direct communications may be provided between two or more of the above components. For example, the network may be based on a combination of WiFi Mesh and Beacon or a combination of WiFi and BLE Beacon. However, other communication techniques can also be used. The direct communications may occur without requiring any intermediary device or network. Indirect communications may be provided between two or more of the above components. The indirect communications may occur with aid of one or more intermediary device or network. For instance, indirect communications may utilize a telecommunications network. Indirect communications may be performed with aid of one or more router, communication tower, satellite, or any other intermediary device or network. Examples of types of communications may include, but are not limited to: communications via the Internet, Local Area Networks (LANs), Wide Area Networks (WANs), Bluetooth, Near Field Communication (NFC) technologies, networks based on mobile data protocols such as General Packet Radio Services (GPRS), GSM, Enhanced Data GSM Environment (EDGE), 3G, 4G, 5G or Long Term Evolution (LTE) protocols, Infra-Red (IR) communication technologies, and/or Wi-Fi, and may be wireless, wired, or a combination thereof. In some embodiments, the network may be implemented using cell and/or pager networks, satellite, licensed radio, or a combination of licensed and unlicensed radio. The network may be wireless, wired, or a combination thereof.

Automated Workflow Control

Figure 8:
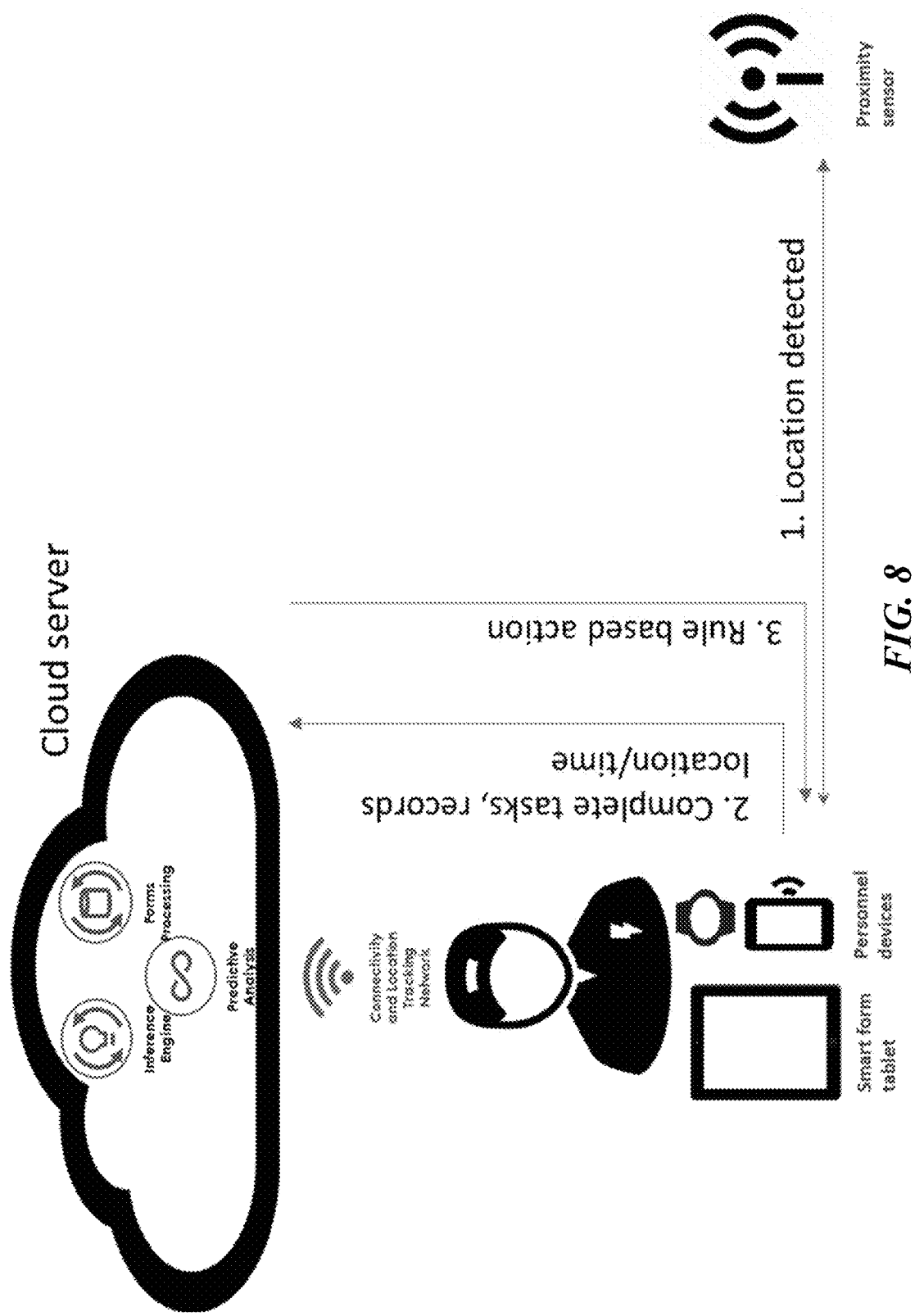
FIG. 8 schematically shows an example process for controlling a workflow, in accordance with some embodiments of the invention.

FIG. 8 schematically shows an example process for controlling a workflow, in accordance with some embodiments of the invention. In the illustrated example, the real-time location of an individual may be tracked and the location data may be used to generate a step-by-step workflow for the individual and provide the assurance of completeness and accuracy of the workflow. For example, when the operator is detected to be within a proximity of a work zone (e.g., detected by a proximity sensor) where an operation/task to be performed, the operation or task may be automatically displayed on the personnel device prompting the operator to complete the task. Alternatively or in addition to, an operator may be permitted to view a series of tasks or set of tasks in different view. For example, an operator may view previous tasks and future tasks, or view tasks assigned to other members in the same project. In some cases, the operator may be prompted to provide input on a smart form delivered on the smart form tablet indicating a completion of the task. In some cases, the user input may also comprise information such as location, time and the context/content of the task. Alternatively or in addition, a user may be requested to provide a simple user input such as a click on the screen, then other information such as the time and the context/content of the task may be automatically generated and filled-in by the system. In some cases, a completion of a task may be automatically detected and confirmed without user intervention. For instance, data collected from the one or more sensors (e.g., motion sensor, proximity sensor, etc.) may be analyzed and determine that a task has been completed by a user.

In some cases, the form or user input data may be transmitted to the edge computing system and/or the cloud. In response to receiving the user input data, the next action or task to be performed may be generated. The steps or operations may be generated based on predetermined rules. Alternatively or in addition to, the steps or operations may be generated using a trained predictive model downloaded from the cloud.

Figure 9:
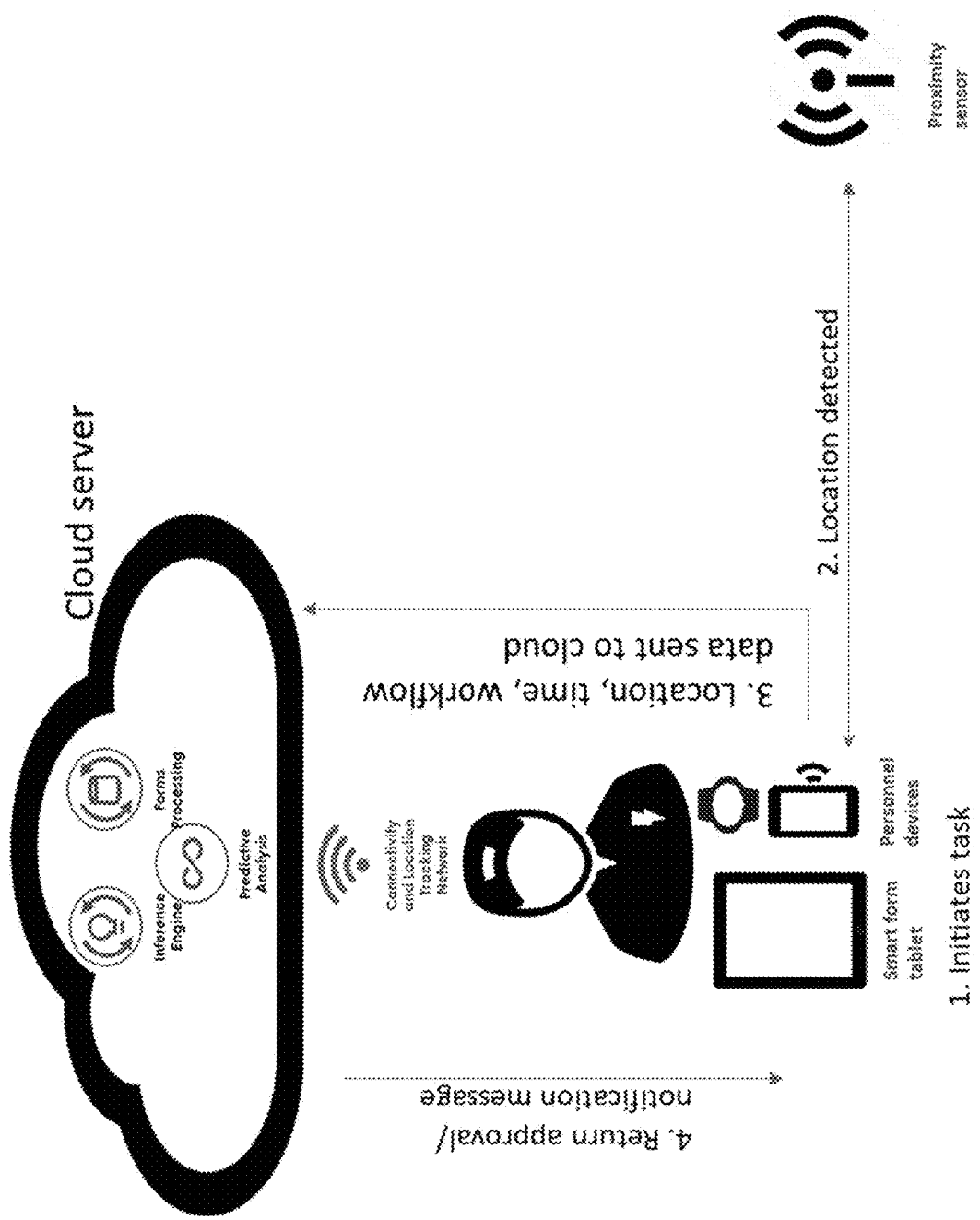
FIG. 9 shows an example process of performing tasks onboard a vessel.

FIG. 9 shows another example process of performing tasks onboard a vessel. In some cases, an individual may initiate an operation, task or action that is not in the pre-generated workflow. The system may allow an individual to submit a request for performing a task via the personnel device or smart form tablet. The request along with the location data may be transmitted to the edge computing system or the cloud for approval. The request may include, for example, contextual data about the task, location and timing of the task to be performed, and the user to perform the task. In some cases, at least a portion of the request may be generated automatically based on sensor data. For example, the location of the task may be generated based on the real-time location of the user/user device. The request can include any other type of request based on the project and work. For example, the request may be about declining a task assigned to the operator. In some cases, the user-initiated task may be approved or denied by a manager or other authorized user who is supervising the operations via a dashboard provided by the edge computing system. In some cases, the edge computing system may automatically determine whether to approve the user-initiated task using a predictive model based on real-time conditions. For example, if the task is initiated in response to the detection of an emergency, the edge computing system may determine whether to approve the task based at least in part on the environment conditions detected by one or more sensors deployed on the vessel. In the example, the operator may receive a message, notification and the like indicating approval of the task via the user device or personnel device.

Figure 10:
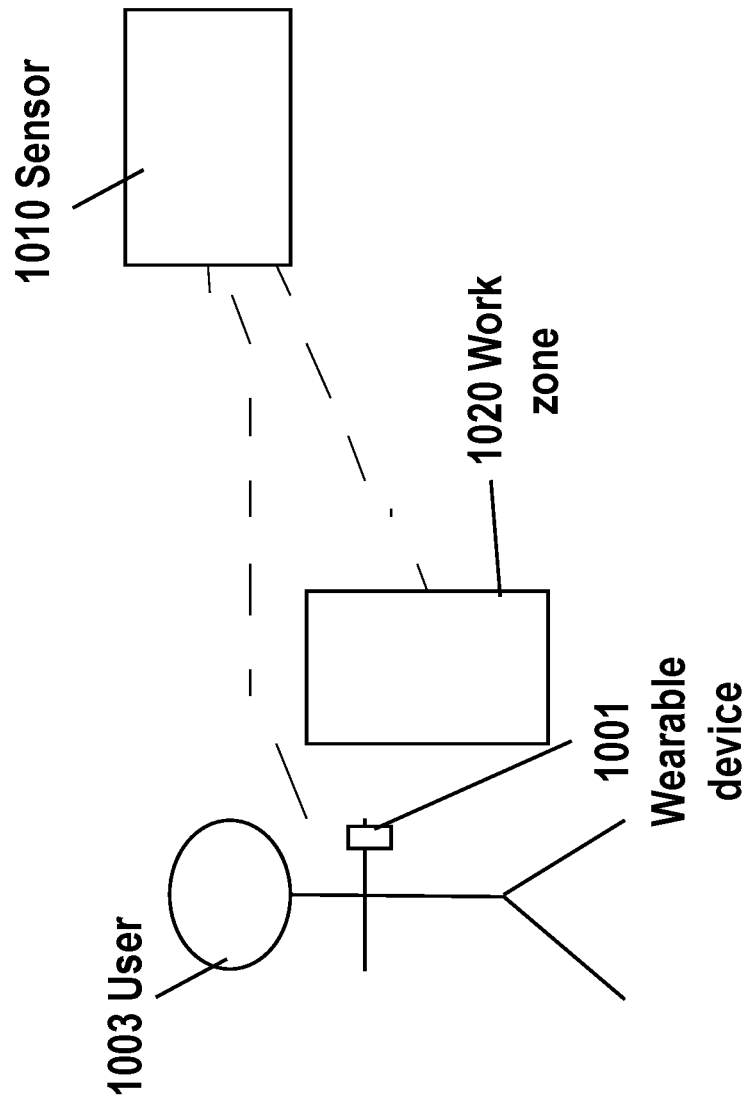
FIG. 10 schematically shows a location-time-based workflow control functionality provided by the safety and risk management system.

FIG. 10 schematically shows a location-time-based workflow control function provided by the safety and risk management system. An individual 1003 may be provided with a wearable device 1001. The wearable device 1001 may work in conjunction with one or more sensors 1010 (e.g., imaging device, proximity sensor, etc.) to detect a location of the user relative to the workplace (e.g., vessel) as described elsewhere herein. For example, a location of the user may be determined with aid of a plurality of Beacon devices deployed in a work zone at a worksite. Any number of sensors for determining the real-time location of the individual can be deployed in a zone. In some cases, a map of the workplace along with the deployment of the sensors may be generated and stored in a database. A worksite can have various regions or work zones which can be associated with one or more sensors deployed therein. In some cases, the position of the individual may be detected using the Bluetooth Low Energy (BLE) beacons that transmit a continuous stream of packets that are picked up by a BLE sensor on the mobile device or the wearable device. The wearable device or the mobile device may be BLE compatible so as to determine the individual's relative physical location to a beacon. Based on ranging data or approximate distance between user's device to each beacon along with the unique beacon's properties, different level of positioning accuracy can be achieved.

In some cases, when an individual is detected to be within a work zone or within proximity to the work zone 1020 where a task to be performed, a message or notification indicating the corresponding action or task may be delivered to the user for completion.

In some cases, the safety and risk management system may provide authentication features to perform operations on the vessel. For example, only authenticated and authorized individual may be permitted to perform a task in compliance with the safety law. The authentication of the individual may be performed via one or more interaction channels, such as wireless, IR, or visible light signal, visual pattern (e.g., similar to QR code), RFID, or other electromagnetic systems. For example, the individuals may have one or more devices that may emit a signal detectable by the machines, and that may authenticate the individuals. In another example, the individuals may provide a password or phrase that may be recognized by the machines. Similarly, an image may be captured of the individuals, and if their face or appearance matches that of pre-approved personnel they may be provided access. Similarly, a fingerprint, handprint, retinal scan, or other biometric data may be used to authenticate the individual and provide them with access to the work zone.

Adverse Event Detection

Figure 11:
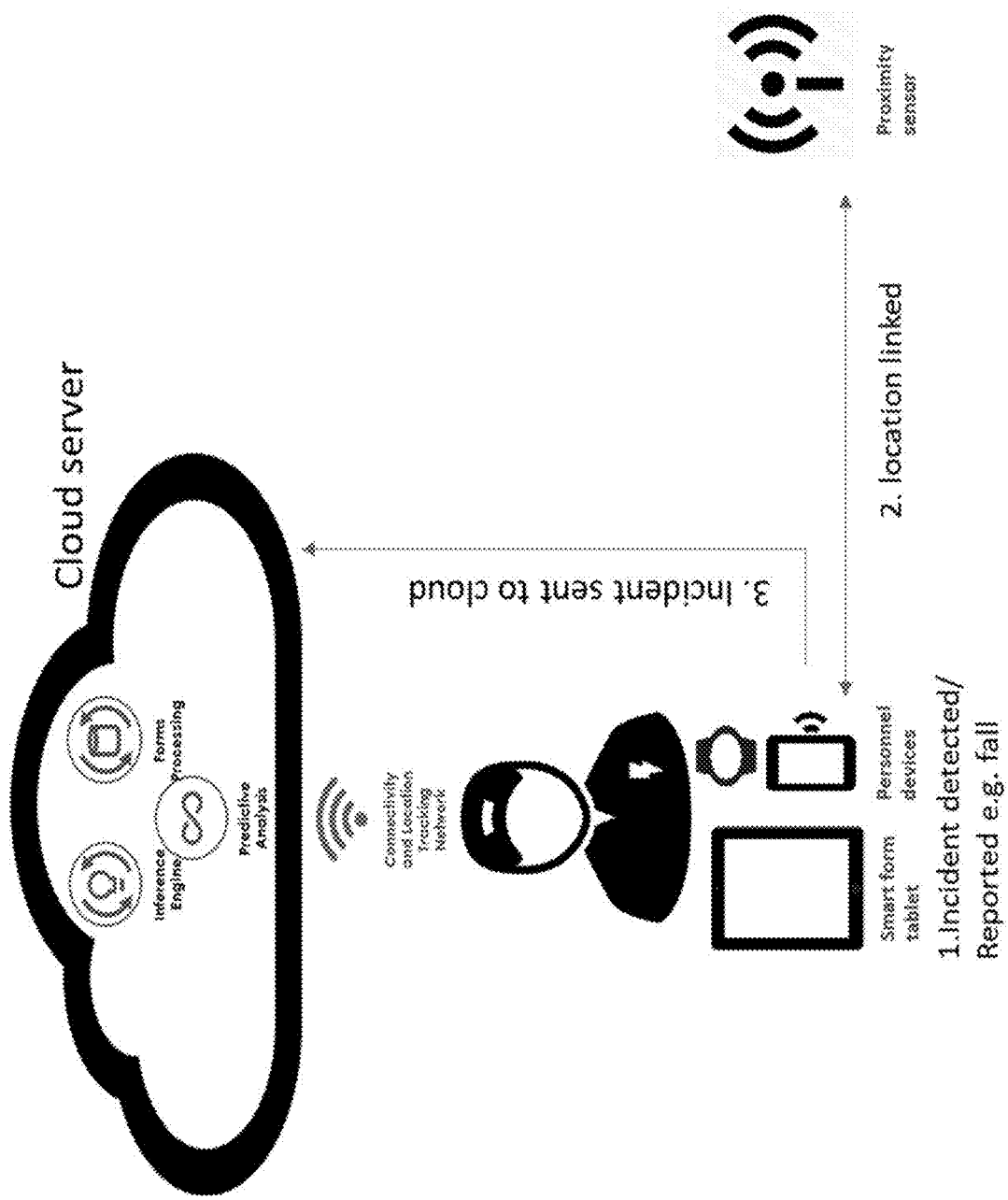
FIG. 11 shows an example process of detecting an adverse event such as trip, slip or fall of an individual.

FIG. 11 shows an example process of detecting an adverse event such as trip, slip or fall of an individual. In some cases, an adverse event may be detected based on sensor data collected by the one or more sensor located on the individual's body (e.g., attached to skin), a part of body (e.g., wearable device) or clothing, and/or sensors deployed in the workplace (e.g., camera). The sensor data may be processed by a machine learning trained algorithm to identify an adverse event such as trip, slip or fall of the individual. The adverse event detection may utilize any suitable gesture detection or gesture analysis techniques that can analyze input data from the user device and/or wearable device in order to detect and/or monitor a predetermined gesture (e.g., trip, fall, or slip). For example, sensor data (e.g., motion data, accelerometer data, physiological data, biometric data, etc.) may be analyzed to determine a probability of the user performing a predefined gesture.

In some cases, in response to a detected adverse event, an alert or message may be automatically generated along with the location and time of the event, and transmitted to the edge computing system or the cloud. In some cases, in addition to the location and time information, information about the detected event such as fall on the deck or fall into the water may also be generated automatically. This functionality can also be used to determine the causes of accidents in a workplace, or to make predictions about workplace accidents. In some cases, a user may be prompted to confirm or deny the occurrence of the event via a GUI. The user may provide input (e.g., confirm or deny) by directly touching the screen (e.g., touchscreen). The user may touch any portion of the screen by touching a point on the screen. For example, a user may confirm the detected event by tapping on a 'confirm' button or deny the event by tapping on a 'deny' button. In some cases, such user feedback data may be utilized to perform continual training of the predictive model to improve the model performance.

Rest and Fatigue Management

Figure 12:
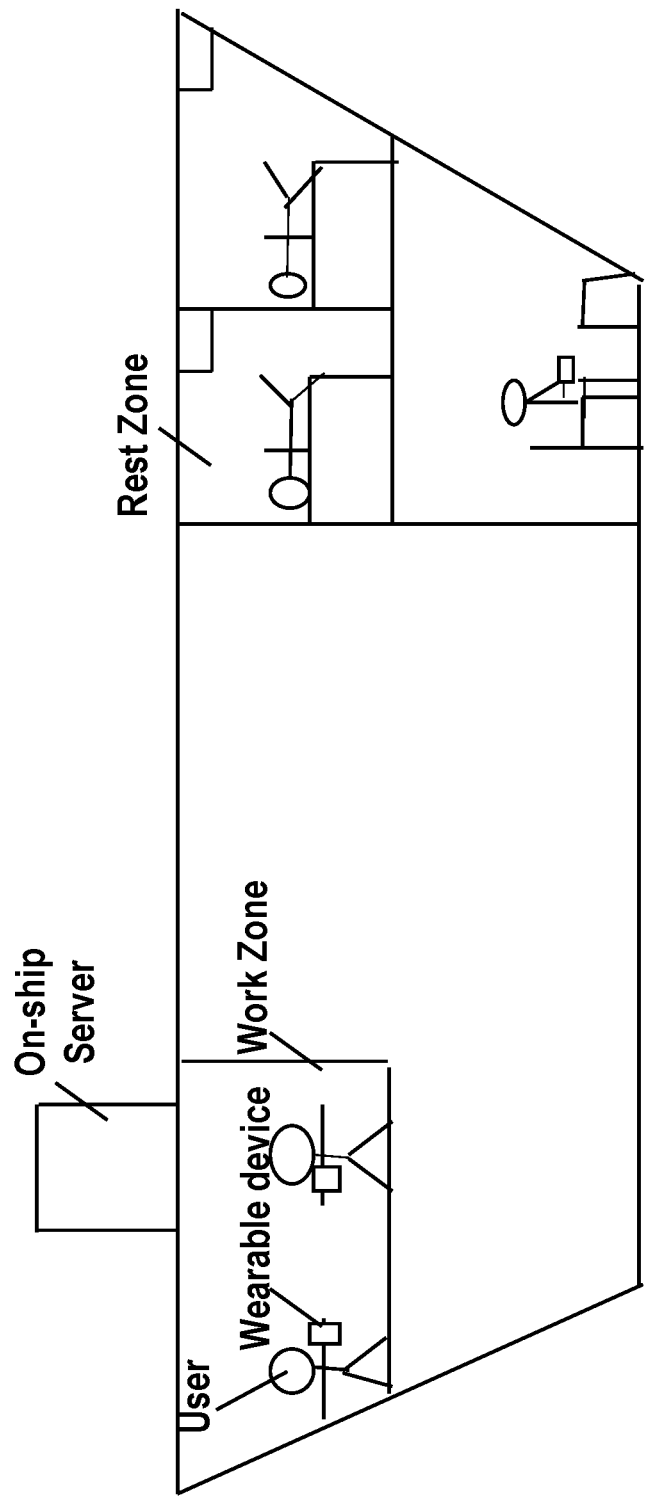
FIG. 12 shows an example of fatigue detection and management.

FIG. 12 shows an example of fatigue detection and management. The safety and risk management system may be capable of monitoring and detecting a fatigue level, sleep-urge, occupational-health sleepiness risks and the like based on real-time sensor data. This may beneficially improve the optimal performance, energy of individuals, and efficiency of work assignment. For example, the edge computing system may analyze the biometric data, physiological data, motion data and the like collected from the wearable device or personnel device to determine the physiological state of an individual (e.g., under stress, fatigued, etc.). The fatigue level may be detected using any suitable analysis techniques such as using a trained predictive model to process the real-time motion data and/or biometric data.

The safety and risk management system may utilize sensor data and a trained predictive model to detect a physiological state such as a fatigue or stress level, provide intervention to the individual or other interested parties (e.g. a supervisor may be alerted when the individual misses the alert), to block a user from being able to access certain systems (e.g. after detecting a change in gait coupled with a temperature change, a signal is sent to nearby heavy machinery to block access to the individual), to allow a user to access systems (e.g. an individual was blocked because of flu but their temperature is normal), to suggest behavioral changes to avoid an accident (e.g. after eye tracking indicates fatigue, the user is signaled, buzzed with a suggestion to take a break), and the like.

The fatigue management component can also be used for generating work assignment. For example, suggestions can be provided to managers based on the analysis to assign individuals with different energy levels to different types of tasks where they can be used most efficiently. The fatigue management component may process the real-time sensor data (e.g., location data, motion data, visual data, physiologic data such as heart rate, galvanic skin response, motion sensor, and/or respiration data, auditory data, etc.) to determine a biometric condition of a user (e.g., a user has been active/inactive for a certain period of time, a user has reached a fatigue level or limit, etc.) and may further be analyzed to determine various suggestions related to work assignment (e.g., rest schedule, a user needs to wake up at certain time, a user should go to sleep as it is a certain time).

Work Rest Hours Tracking

The safety and risk management system may be capable of tracking and recording an individual's (e.g., crewman's) daily working hours and rest hours based on real-time sensor data. This may beneficially improve the optimal performance, energy of individuals, and efficiency of work assignment. The safety and risk management system allows for accurate, automated recording of crewman's daily working hours on vessel. For instance, one or more work zones and rest zones may be pre-designated, then information about when an individual has started work and when an individual has finished work in conjunction with ongoing involvement with task or workflows may be captured using the location/movement tracking method (e.g., wearables device, BLE beacons) as described elsewhere herein. The total number of hours worked may be automatically calculated and then tracked against the industry work/rest regulations and against upcoming work schedules. In instances of potential overwork, a warning signal may be generated and in some cases, interventions can be proactively suggested. For example, the interventions may include adjustment of workload management (e.g., reduction in upcoming work hours) and/or matching suitably qualified substitutes from the ship's crew. The substitutes may be selected based on crew rank/work profiles, availability and recent working hours of the candidate substitutes or other factors.

In some cases, the working hours and/or rest hours may be determined using a trained predictive model. For example, a trained predictive model may process the real-time motion or location data and output predicted working hours and/or rest hours of the individual. In some cases, other sensor data such as biometric data may also be captured and used to determine the working hours and/or rest hours or quality of rest (e.g., sleep quality). In some cases, the fatigue level analyzed by the fatigue management component may be used in conjunction with the work rest hours tracking component to determine an optimal work rest hours schedule and/or tasks assignment for a single crewmember or a group of crewmembers.

In some cases, work and rest hours data may be captured using a wearable device and the total sum of work and rest hours over multiple time periods may be calculated to track and alert a supervisor through a supervisory dashboard in real time about potential violations by a crew member of rules stipulated by international labor organizations such as International Labor Organization (ILO). This functionality provides supervisor with a real time visibility into crew work and rest data to pre-emptively avoid any violations of work/rest rules and manage work related fatigue levels of the crew through the improved planning and workload management.

Example of User Interfaces

In some embodiments, the provided safety and risk management platform may generate one or more graphical user interfaces (GUIs). The GUIs may be rendered on a display screen on a user device (e.g., dashboard tablet, digital form tablet) or a personnel device (e.g., mobile device). A GUI is a type of interface that allows users to interact with electronic devices through graphical icons and visual indicators such as secondary notation, as opposed to text-based interfaces, typed command labels or text navigation. The actions in a GUI are usually performed through direct manipulation of the graphical elements. In addition to computers, GUIs can be found in hand-held devices such as MP3 players, portable media players, gaming devices and smaller household, office and industry equipment. The GUIs may be provided in a software, a software application, a web browser, etc. The GUIs may be displayed on a user device (e.g., mobile device, wearable device, sensory device, etc.). The GUIs may be provided through an application running on the user device or personnel device.

Figure 13:
FIG. 13 shows example GUIs rendered on different electronic devices.

FIGS. 13-17 show examples of various GUIs provided by the safety and risk management system. FIG. 13 shows example GUIs rendered on different electronic devices. The GUI may be rendered on a user device or personnel device carried by an individual. The GUI may also be rendered on an edge device or host device that may be accessed by a supervisor or manager. The edge device, the user device and the personnel device may be a computing device that can display one or more GUIs. The edge device, the user device and the personnel device can include, among other things, desktop computers, laptops or notebook computers, mobile devices (e.g., smart phones, cell phones, personal digital assistants (PDAs), and tablets), and wearable devices. The wearable device may be, for example, smartwatches, wristbands, glasses, gloves, headgear (such as hats, helmets, virtual reality headsets, augmented reality headsets, head-mounted devices (HMD), headbands), pendants, armbands, leg bands, shoes, vests, motion sensing devices, etc. The edge device, the user device and the personnel device may include known computing components, such as one or more processors, and one or more memory devices storing software instructions executed by the processor(s) and data.

In the illustrated example, a user may receive a notification within the GUI indicating an event is detected. A user may be presented with a smart form on a smart form digital device. A user such as a manager or supervise may review a dashboard GUI displaying live information about the vessel, operations and personnel on the vessel. The GUIs accessed by the manager and crewmembers may be the same. Alternatively or in addition to, different GUIs may be accessed by users with different authorization levels.

A user may interact with the GUI through direct touch on a screen or IO devices such as handheld controller, mouse, joystick, keyboard, trackball, touchpad, button, verbal commands, gesture-recognition, attitude sensor, thermal sensor, touch-capacitive sensors, or any other device. The GUI may enable a user to interact with systems of the disclosure, such as for visualizing an alert or notification about a result generated by the model system and providing user input about the result. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input.

Figure 14:
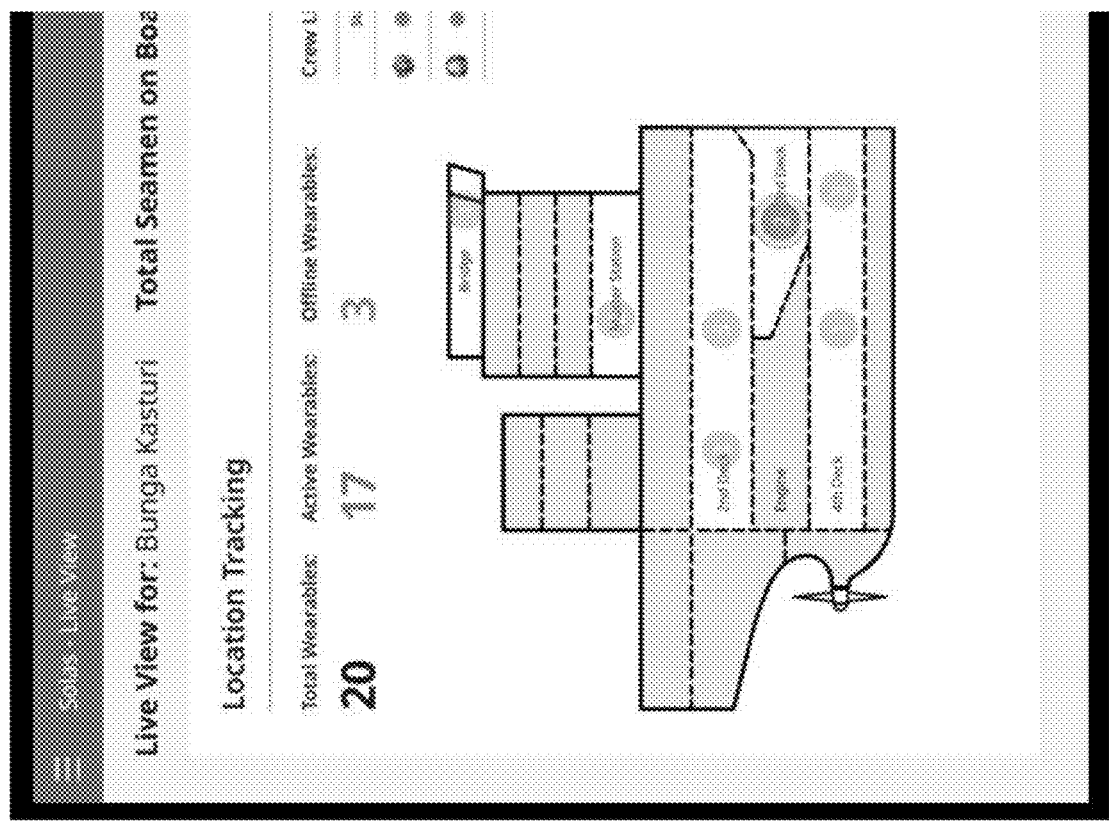
FIG. 14 shows an example GUI displaying a dashboard.

FIG. 14 shows an example GUI displaying a dashboard. In the example, the dashboard may display real-time information about the worksite (e.g., vessel), one or more local devices (e.g., wearable devices, mobile device, user devices) in the local network and locations of the devices at the worksite. The dashboard may display the real-time location of the devices and the associated individuals at the worksite. For example, identity of the individual, title, or permission level of the individual may be viewed through the dashboard. This may beneficially show the real-time condition such as an occurrence of emergency event, status of operations and individuals on the vessel.

Figure 15:
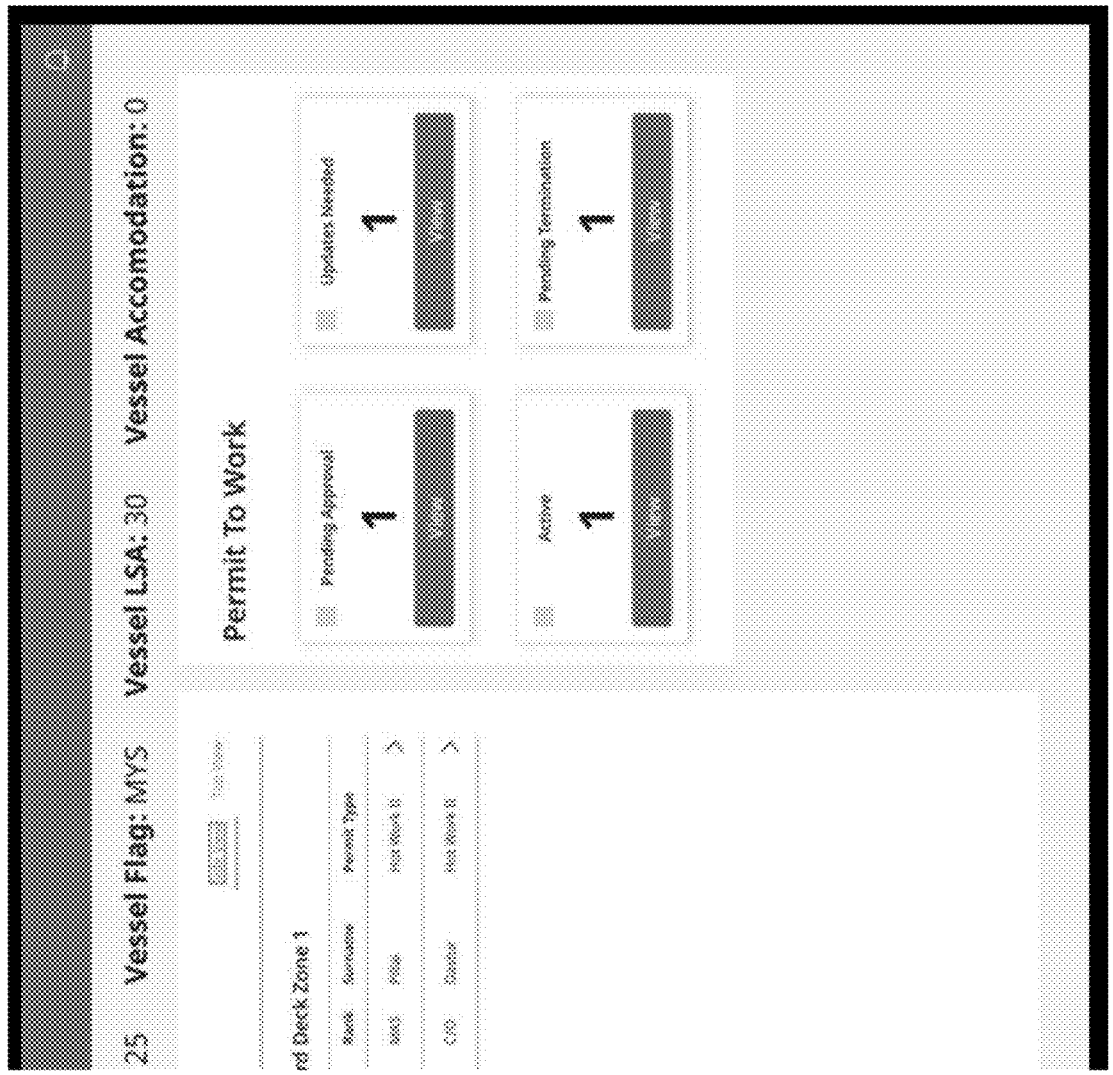
FIG. 15 shows an example GUI for a manager or supervisor for control of work management.

FIG. 15 shows an example GUI for streamlined approval management. The GUI may be accessed by a manager or supervisor. The GUI may show actions or operations performed on the vessel. For example, a type of the operation, operator and status of the operation may be displayed. The GUI may receive user input to modify permission status of a work. For example, a user (e.g., manager) may be prompted to view 'pending approval' of work to be performed, and the user may confirm or deny a request for approval a work via the GUI. The user may provide input (e.g., confirm or deny) by directly touching the screen (e.g., touchscreen). The user may touch any portion of the screen by touching a point on the screen.

Figure 16:
FIG. 16 shows an example GUI rendered on a user device.

FIG. 16 shows an example GUI rendered on a user device. The GUI may display a smart form showing information about operations to be performed by an operator or user of the device. For example, when an operator is detected to be within a proximity of a work zone, a task may be displayed on the GUI and the operator may be prompted to confirm on the GUI upon completion of the task.

Figure 17:
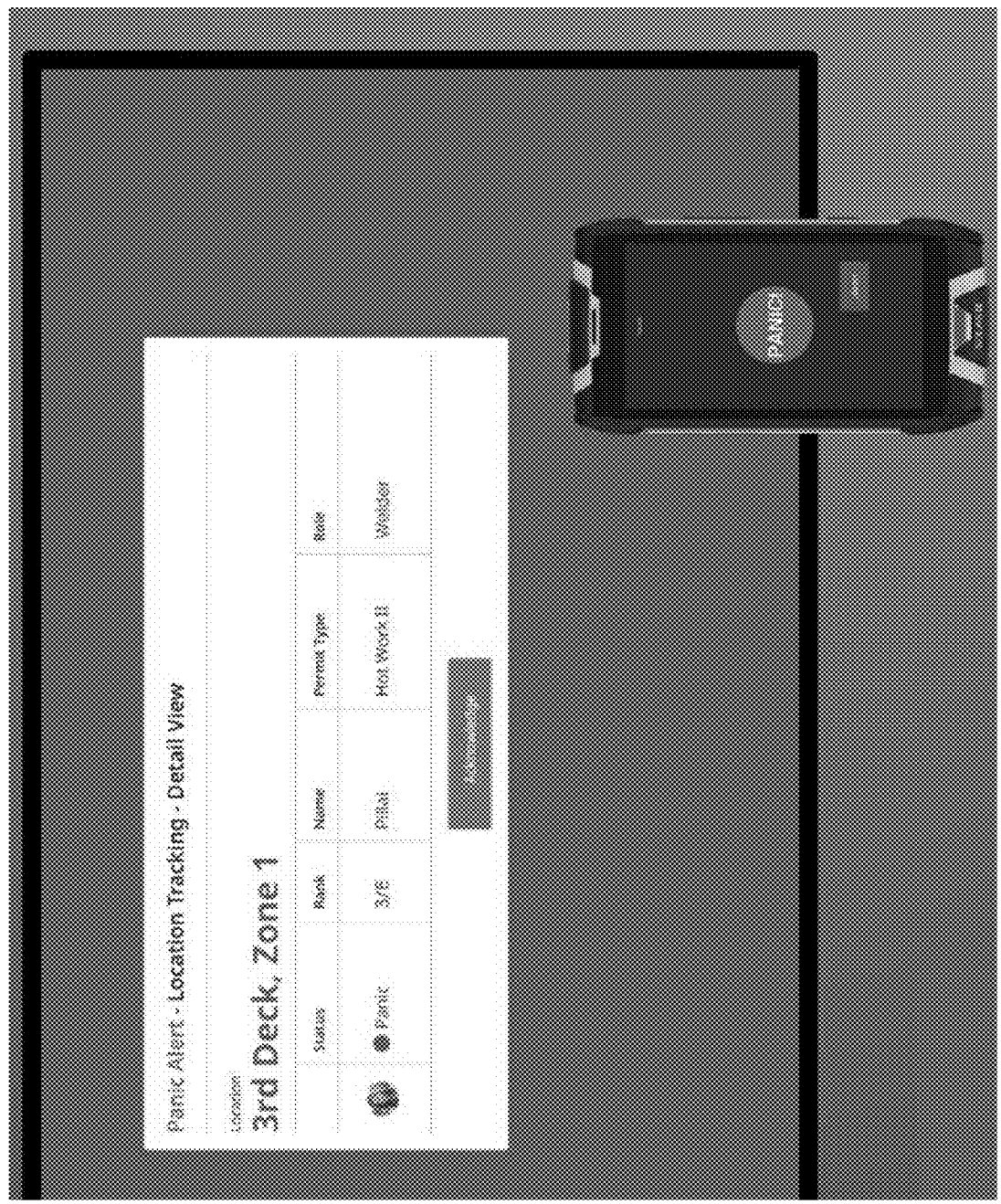
FIG. 17 shows an example GUI for alerting an emergent event.

FIG. 17 shows an example GUI for alerting an emergent event. For example, a GUI may be rendered on a host dashboard showing panic alerts. The alert may comprise information about the location of the emergency event, the individual who triggered the alert, and the type of event (e.g., panic). An individual or operator may also be permitted to trigger a panic alert via a user device or personnel device. The alert may be transmitted instantly to the edge computing device and delivered to the supervisor, manager or other crewmembers.

Figure 18:
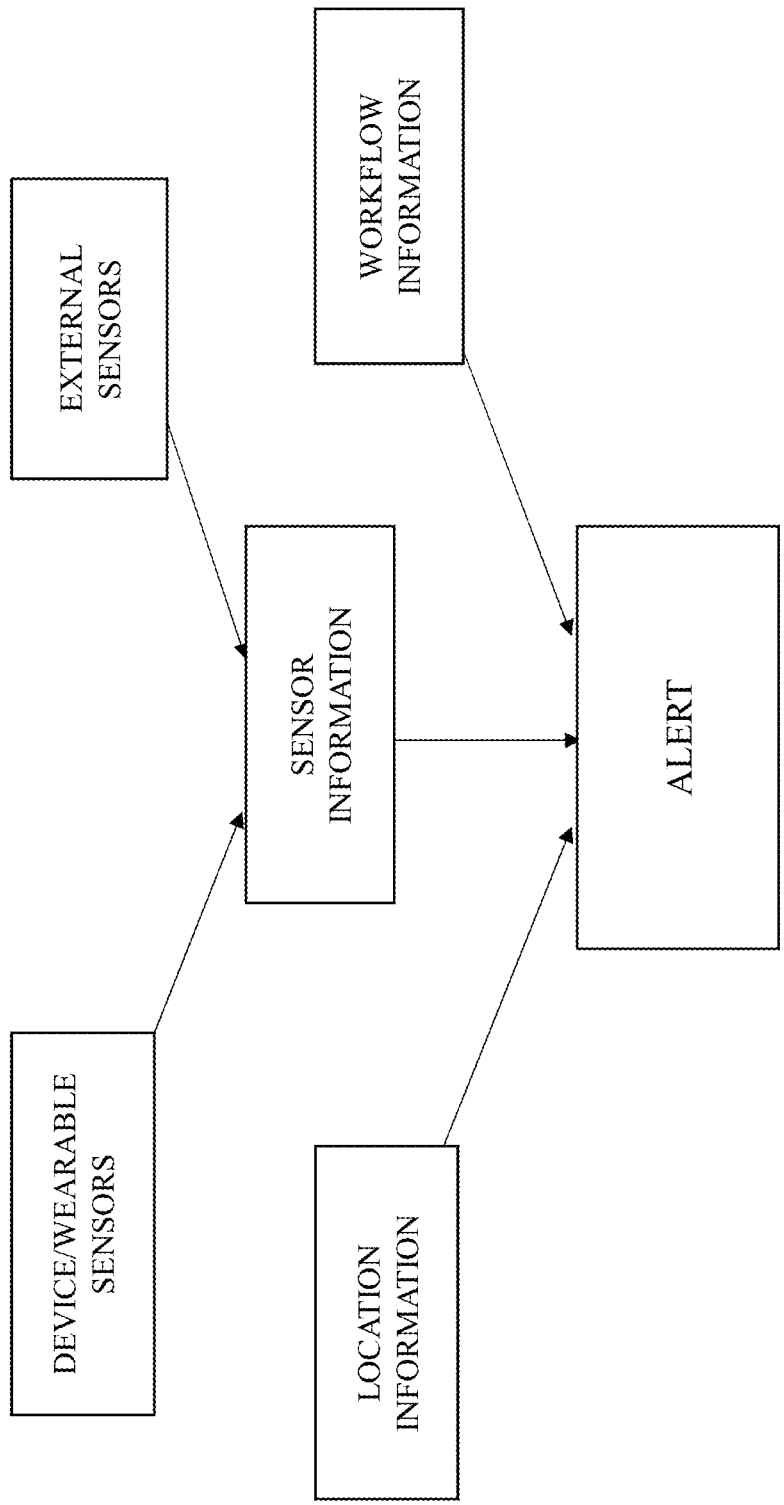
FIG. 18 schematically shows the data flow for generating an emergency alert.

FIG. 18 schematically shows the data flow for generating an emergency alert. The safety and risk management system may be capable of generating an alert in response to the detection of an emergency event. For example, sensor data collected from the wearable device, user device and external sensors may be processed to determine an emergency event (e.g., trip, fall, slip, etc.). In another example, an alert may be triggered by an individual via direct user input. The alert may be generated with location information about the event, the related individual, and the status of the individual. In some cases, the status of the individual may be derived from the workflow information such as the operation that is currently performed by the individual. In some cases, in addition to alerting an emergency event, selected crewmembers or manager may be notified and navigated to the emergency site via the safety and risk management system. For instance, when a panic alert is triggered, one or more crewmembers may be dispatched to the emergency location based on instantaneous location and availability of the crewmembers on the vessel.

Figure 19:
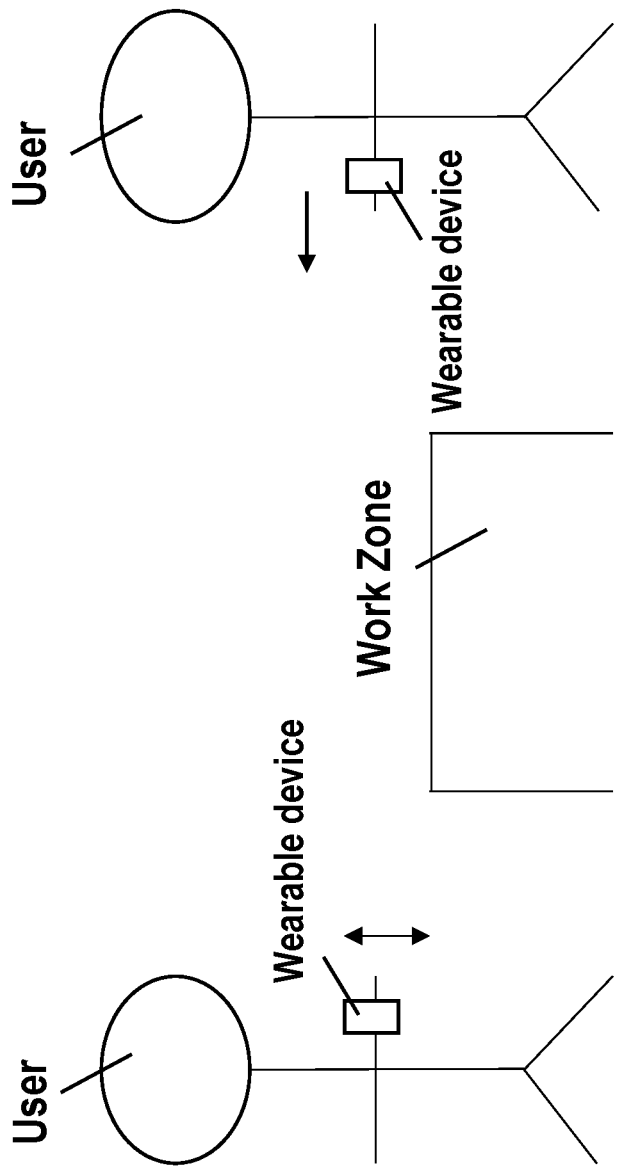
FIG. 19 schematically illustrates assignment of work among a group of individuals.

FIG. 19 schematically illustrates assignment of work among a group of individuals. In some instances, a group of operators can be assigned to a task. More than one operator can be assigned to the task, for example, at least about 2, 3, 4, 5, 6, 7, 8, 9, or 10 operators can be assigned to work collaboratively on a single task. With the aid of the dashboard tablet, the manager onboard can allocate the right amount and right level of experience to attend to each task. The sensor data can be analyzed to determine if the group of operators is being efficient at performing the task. The sensor data can be analyzed to determine the optimal number of workers and/or an optimal schedule, workflow assigned to the task. In some cases, the group of operators may also be assigned upon detection of an emergency event as described above. In some cases, one or more operators may be detected to be within proximity of a work zone to perform one or more tasks. A message or notification indicating the corresponding action or task may be delivered to the user for completion or a smart form may be displayed on the user device.

Figure 20:
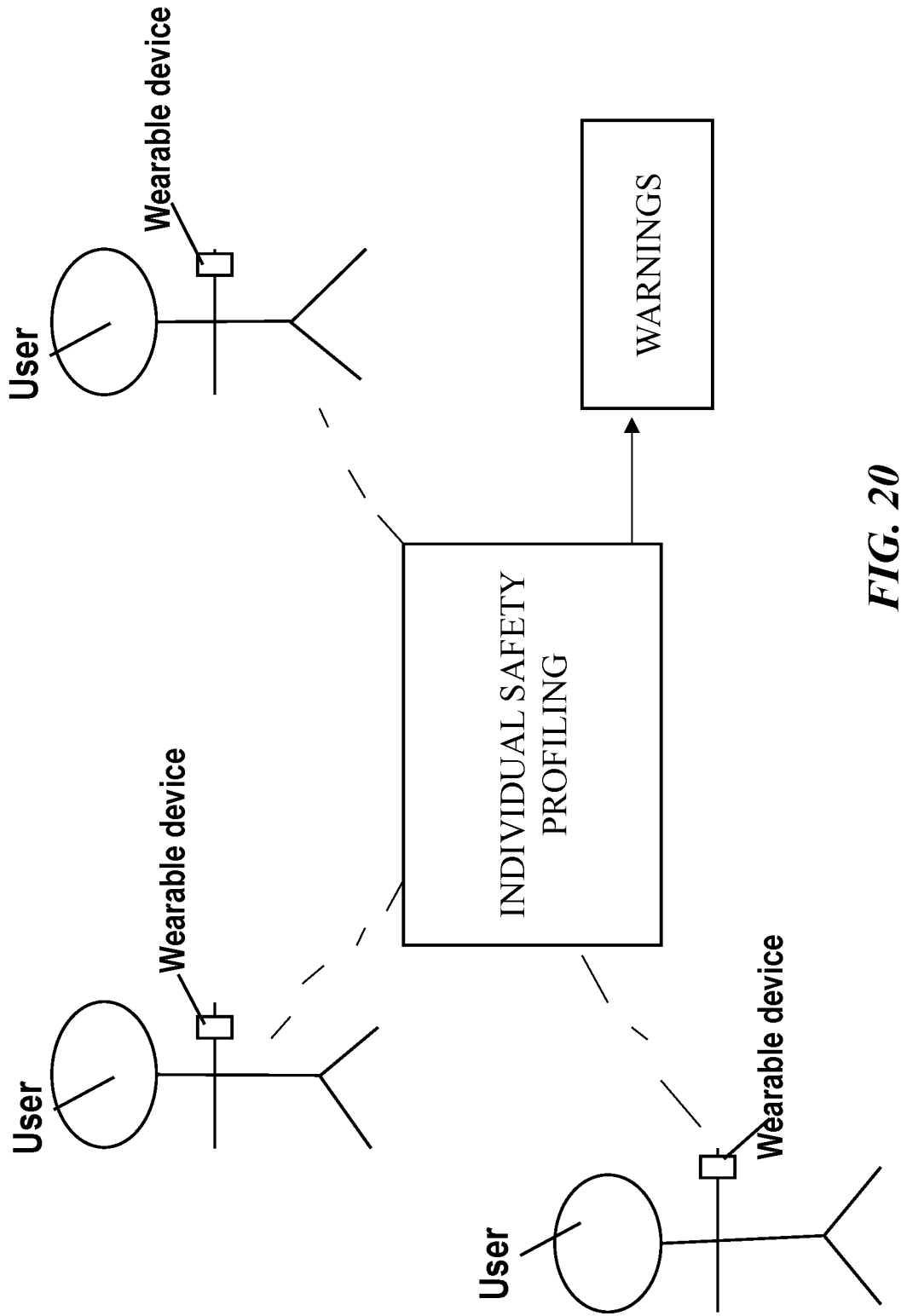
FIG. 20 schematically illustrates an individual safety profiling module provided by the safety and risk management system.

The safety and risk management system may be capable of generating a safety profile for each individual. FIG. 20 schematically illustrates an individual safety profiling module provided by the safety and risk management system. The safety profile for an individual may be generated based on a workflow completed by the individual and real-time conditions. For example, the safety profile may comprise a series of operations have been performed and to be performed in specific locations and time points. In some cases, warnings about a hazardous condition in a worksite may be generated and delivered to the individual prior to the individual entering the hazardous work zone. The hazardous condition may be detected based on sensor data collected from various sensors deployed in the workplace (e.g., temperature sensor, chemical sensor, etc.). In some cases, an impeding hazardous event or hazardous condition may be predicted or forecasted. For example, the safety and risk management system may be capable of forecasting an impeding adverse event a certain timespan before the occurrence of the event. The forecasting or prediction of an impeding adverse event may be generated using a trained model.

In some embodiments, the system may generate a Health Index to provide holistic measure of health and wellbeing of individuals (e.g., seafarers and industrial workers) based on an exposure to occupational risk factors that have been known to adversely affect the safety, health and wellbeing of workers. The Health Index may be calculated based on an exposure level to hazards that affect health and wellbeing of workers. This exposure level to hazards may be determined based on data collected via the variety of sensors on the wearable device, user data (e.g., type of work that a worker is involved in), data collected from the work flow management component and various of other data managed by the system. The Health Index may be calculated based on a variety of factors such as time spent in a high hazard geofenced area, work rest hours, and personal wellness conditions such as heart rate, type of job performed, fatigue level and various others. For example, the health index may be calculated based on a variety of working conditions such as long working hours resulting in fatigue, lack of rest, exposure to hazardous and toxic environments, exposure to high heat and noise, exposure to vibration, physical safety hazards, heart rate variability, heart rate spikes, resting heart rate, step counter, and the like. The Health index may quantify a health and wellbeing condition of an individual. In some cases, when the Health index value (e.g., a score) indicating anomalies or regular occurrence of spikes, workers may be advised to consult with their doctors.

The system may be capable of determining an occupational risk exposure level for an individual. The system may use historical location data of an individual to determine the exposure levels to occupational risks, including such as frequency of exposure to areas with toxic substances, areas with high noise levels, areas with high vibration levels, areas with high heat index with a potential risk of causing heat stress to the individual and the like. Such exposure levels to occupational risks may be used to devise programs and policies to target certain tasks-related roles and ranks that undergo high occupational risk to mitigate the risk levels.

For instance, the system may use the crew/work data collected from the work flow management component such as "working on heights", "hot work", "cold work", "underwater operation", and the like to determine the exposure levels to risks for crew members. The exposure level may be estimated based on the individual's job history that adversely affects health and wellbeing of seafarers and/or industrial workers. The exposure levels may be estimated based on the location information collected through the network of devices onboard the vessels or in an industrial workplace.

The system may monitor health vitals (e.g., heart rate) and measure activity levels for individuals. The health vitals may be collected from the physiological sensors on the wearable device. The activity level may be determined based at least in part on counting the number of steps taken during a certain time period. The steps data gathered onboard the vessel from the personal device (e.g., wearable device) may be accessible through the web-based portal. In some cases, users of the system may be permitted to generate reports and may be shared with insurance companies to determine insurance premiums.

The health vitals may include at least heart rate. The system may, for example, monitor heart rate and alert a crew member when the heart rate is detected to be abnormal or beyond certain normal limits. A crew member may be able to share this information with their doctors for further advice and diagnosis via the system. In some cases, the heart rate may be combined with other measures of fatigue such as work rest hours and activity level to generate insights on health and wellness of the individual.

The system may also track the activity level of an individual such as by counting the distance walked by an individual (e.g., step counting). For example, such activity level may be monitored with respect to hazardous/explosion prone environments. For instance, different work zones with different hazardous conditions may permit different levels of activities. The system may measure the activity along with other factors (e.g., Work Rest hours, heart rate and heat stress in real-time) to determine whether a fatigue level of an individual. Additionally, the system may track the activity to incentivize an individual to stay active and healthy. The step counting capability may be enabled by the wearable device or the motion sensors onboard the wearable device (e.g., accelerometer), and appropriate algorithms.

The system may be capable of detecting or monitoring heat stress. Working continuously in a hot and humid environment can lead to exhaustion, fatigue and accidents. The system advantageously provides real-time work environment monitoring and fatigue levels detection accounting for heat. The system may generate a Heat index which is a cumulative indicator of temperature and humidity. For example, the wearable device may monitor the Heat index by monitoring surrounding ambient temperature and humidity. The Heat index may be calculated using any suitable formulas. Prolonged exposure to heat may trigger alerts. For example, an alert may be auto-generated by the system when the exposure to heat is detected to be exceeding a pre-determined threshold. Alerts may appear on the wearable device and/or on a supervisory dashboard. In some cases, an individual may be informed of the surrounding environment (e.g., Heat Index, unsafe zone), and may be presented with details on steps to prevent risk (e.g., heat stress). Supervisors may also be informed of the work conditions of an individual so that they may intervene and take preventive measures to ensure crew safety.

Geofencing

The safety and risk management system may be capable of generating geofencing based on real-time conditions. A geofence is a virtual boundary that may be created based on the sensor data such as GPS, RFID, Wifi or cellular data as described above. The geofencing may integrate information from the safety and risk management system to reduce occupational risk, generate optimal planning, and avoid incompatible jobs from commencing simultaneously.

In some cases, geofencing provided by the system may have a dynamic boundary or barrier determined based on real-time conditions. For example, the system may include a barrier management unit for establishing and maintaining barriers such that to prevent an undesirable incident from occurring or mitigate the consequences should such an incident occur.

In some cases, the geofencing may have a dynamic barrier indicating the location and area/scope of a hazardous work zone. The barrier may be automatically determined based on sensor data collected from a network of sensors (e.g., wearable device, sensors deployed in the workplace, etc.) and a detected hazardous condition. The hazardous condition may be detected based on sensor data collected from various sensors deployed in the workplace (e.g., temperature sensor, camera, etc.) as described above. For example, sensory data from wearable devices or other sensors about environmental condition of a work zone (e.g., heat index of environment may be collected), the system may generate a geofencing area with a boundary corresponding to such work zone and alert individuals when they are detected to be in the geofencing area with prolonged exposure that is beyond healthy exposure limits.

In some cases, a geofencing area may have a dynamic duration. For example, geofence for areas where the risks exist for a short period of time (e.g., temporarily increase temperature, toxic gas leak, malfunction of an equipment, etc.) or associated with a high hazard work or situation due to nature of this work or situation such as helicopter operation, mooring, underwater operation, and the like may have dynamic duration. For such areas, the geofence duration may be set by the system automatically according to the duration of work being carried out (e.g., as specified in the system by an individual/supervisor, different scheduled activities and geofence may automatically update as work tasks progress) or according to a real-time environment condition change or activity change detected by the system. For example, a geofence may be automatically terminated upon detection that a hazardous condition is no longer in presence or an operation has been completed.

In some cases, a permission to enter the geofencing area may be different with respect to different individuals according to their respective safety profile, or other personal or real-time conditions about an individual. For example, individuals may be permitted to enter a geofencing area based on a pre-set permission (e.g., title, permission level, personal crew data), and/or the individual's wellness/health condition monitored by the system. For instance, an individual may not be permitted to enter a geofencing area when the individual is detected to exceed a fatigue level, sleepiness risk level or heat stress level. In some cases, a permission to enter the geofencing area may be determined based on a combination of the individual's real-time health condition and a real-time condition of the geofencing area. For example, a permission for an individual to enter a given geofencing area may change according to a change in the risk level of the geofencing area or a change in the Health Index of the individual. For example, an individual may be permitted to enter a geofencing area when the health condition of the individual meets a requirement to enter the geofencing area with a specific risk level or type of risk.

In some cases, the geofencing area may have a fixed barrier that is defined by a user. The fixed geofencing boundary may be a pre-defined and persistent geofence around areas that have persistent and high occupational risk levels due to persistent nature of hazards associated with the work location. For example, a fixed, pre-defined, and persistent geofence may be created for certain areas in a vessel where there are certain hazards at all times. In another example, the geofence may be permanent and may be active irrespective of whether a hazardous operation is being carried out or not. These areas may be set as hazardous because of potential existence of hazardous substances such as toxic gases as well as due to lack of ventilation.

For the geofencing areas with fixed barrier, the permission to enter or how long an individual is allowed to stay in the area may also be different according to the health condition or a nature of job to be carried out associated with an individual. In some cases, the system may detect unauthorized entry or safety breaches, persons involved may be notified along with their supervisor so that an appropriate intervention can be carried out.

The barrier management unit of the system may provide a variety of geofencing functionalities. For example, work may be planned and sequenced based on job compatibility to ensure that incompatible work does not occur in same locations or in vicinity where it is not safe to carry it out simultaneously. For example, when hot work planned in area A for which work has already commenced and cold work is being scheduled to be done simultaneously in the same area or nearby area, a geofence created for the hot work may alert the Master not to approve the cold work as they are not compatible work types and should not be commenced in the same or nearby areas simultaneously. Another example of the geofencing functionality include monitoring exposure levels to high hazard jobs and hazardous locations. The system may provide high hazard work related information such as location of work, the individual who is going to perform the work, the risks involved, and the like. Such information may be used to determine the exposure levels of the individual and devise programs to manage their exposure levels. For example, the system may track the percentage of time spent in geofenced area where there are high noise levels, and measure the decibel levels. When a higher than permissible exposure limits (PEL) is detected, the system may alert the individual not to exceed an exposure duration. Similarly, a geofence around high heat and humidity (high Heat index) areas may alert an individual to not exceed an exposure duration. The system may generate geofence automatically or permit users to manually generate a geofence based on the nature of job being carried out (e.g., using permission to work information).

As described above, the system may permit users (e.g., supervisors) to manually define a permanent or temporary barrier of a geofence, geofence around a hazardous environment or location of hazardous work. This functionality may provide visibility and proactive awareness of risks in situations where crew may be unaware of the risks and measures to be undertaken when entering a high risk area. In some cases, people without situational information may enter a work area or operations unknowingly, or crew may unknowingly remove a lock-out-tag-out (LOTO) or EIC (Electrical isolation) for a machinery that is currently being isolated, without knowledge and informing the proper authorities. The provide geofencing feature may beneficially ensure positive isolation of the hazard. A geofence may be useful for informing the entrant of a LOTO, alerting of the risks, and informing the appropriate authority of the breach.

Figure 21:
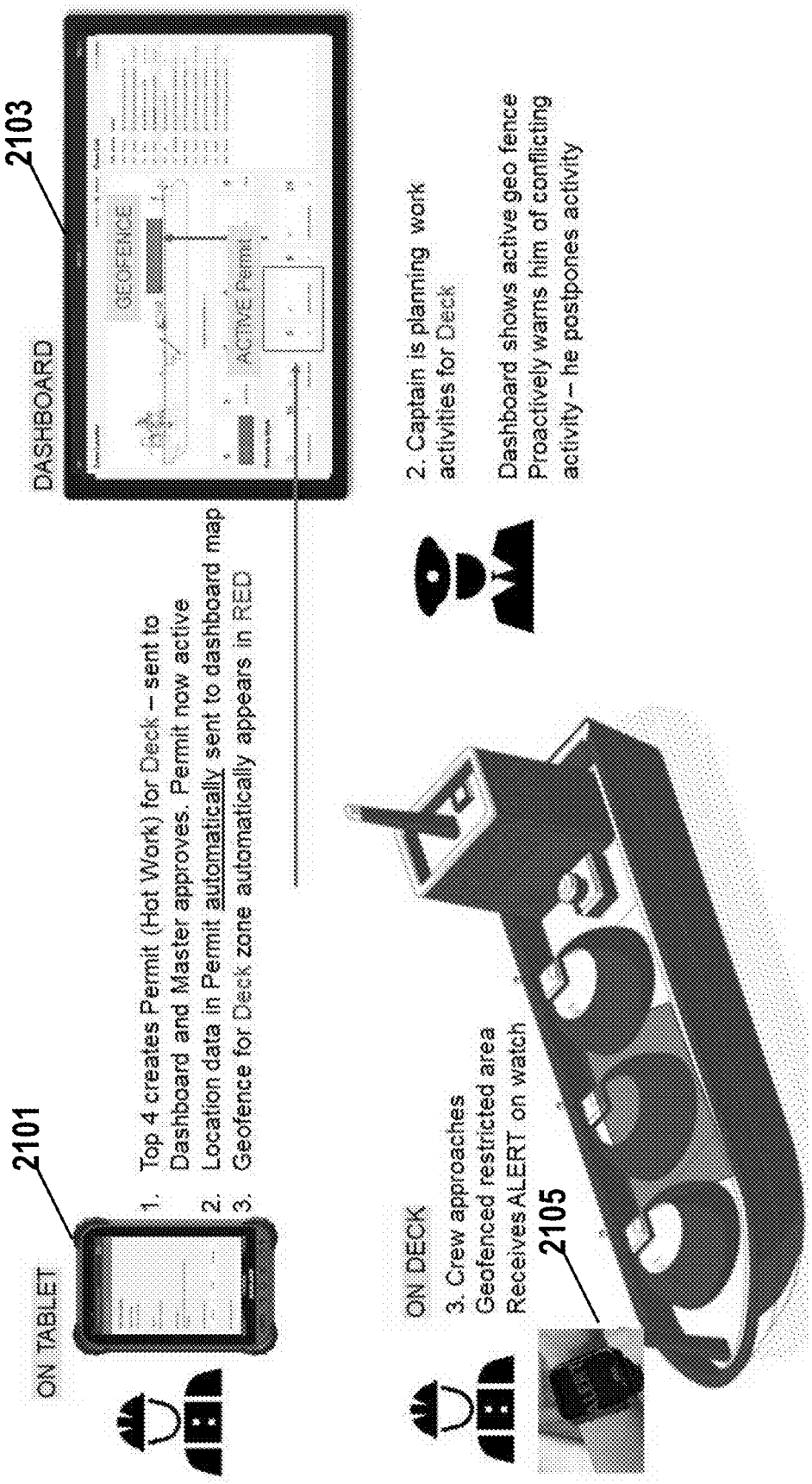
FIG. 21 shows an example of generating and managing a dynamic geofencing using the system.

FIG. 21 shows an example of generating and managing a dynamic geofencing using the system. In the illustrated example, officers/watch keepers on the shipping vessel may assign permission to work for individuals such as based on the detected real-time wellness condition. Alternatively, the permission to work may be automatically updated by the system based on a detected real-time wellness condition. The permission to work associated with the individuals may be entered via the tablet 2101. A Master approves the permit to work. Location data or work zones may be obtained from the work flow management component and sent to three supervisory dashboards located at three locations on the vessel.

Geofence may be created around the work zones and displayed on the supervisory dashboard 2103. Once created, the geofence may be activated and can detect personnel entering the geofenced zone. In some cases, when an individual enters a geofenced zone, the system may detect it and determine whether they are authorized to work in this area based on the permitted work within the area and the permission to work of the individual. If the individual is not authored to enter, an alert may be sent to the individual's wearable device 2105 to alert them that it is a hazardous area and they should leave.

The alert on wearable device 2105 may be delivered using different types of modes such as buzzer sound, modal text message on the wearable, visual alert on wearable, vibration alert on wearable or combination thereof. In some cases, an individual may be permitted to proceed with using the wearable device after they input a command indicating acknowledgement of the alert. An alert may also be sent to the supervisory dashboard 2103 alerting the officers/watch keepers that a breach of geofence has occurred.

The duration of automatically created geofence may be based on the duration or validity of permission to work. When the work is done, the geofence may be automatically disabled or deactivated after which workers may not be alerted upon entering the previously geofenced zone. In some cases, the geofencing area may be automatically created upon detection of a real-time hazardous condition in the environment and the geofence may be automatically disabled when the hazardous condition is diminished.

Figure 22:
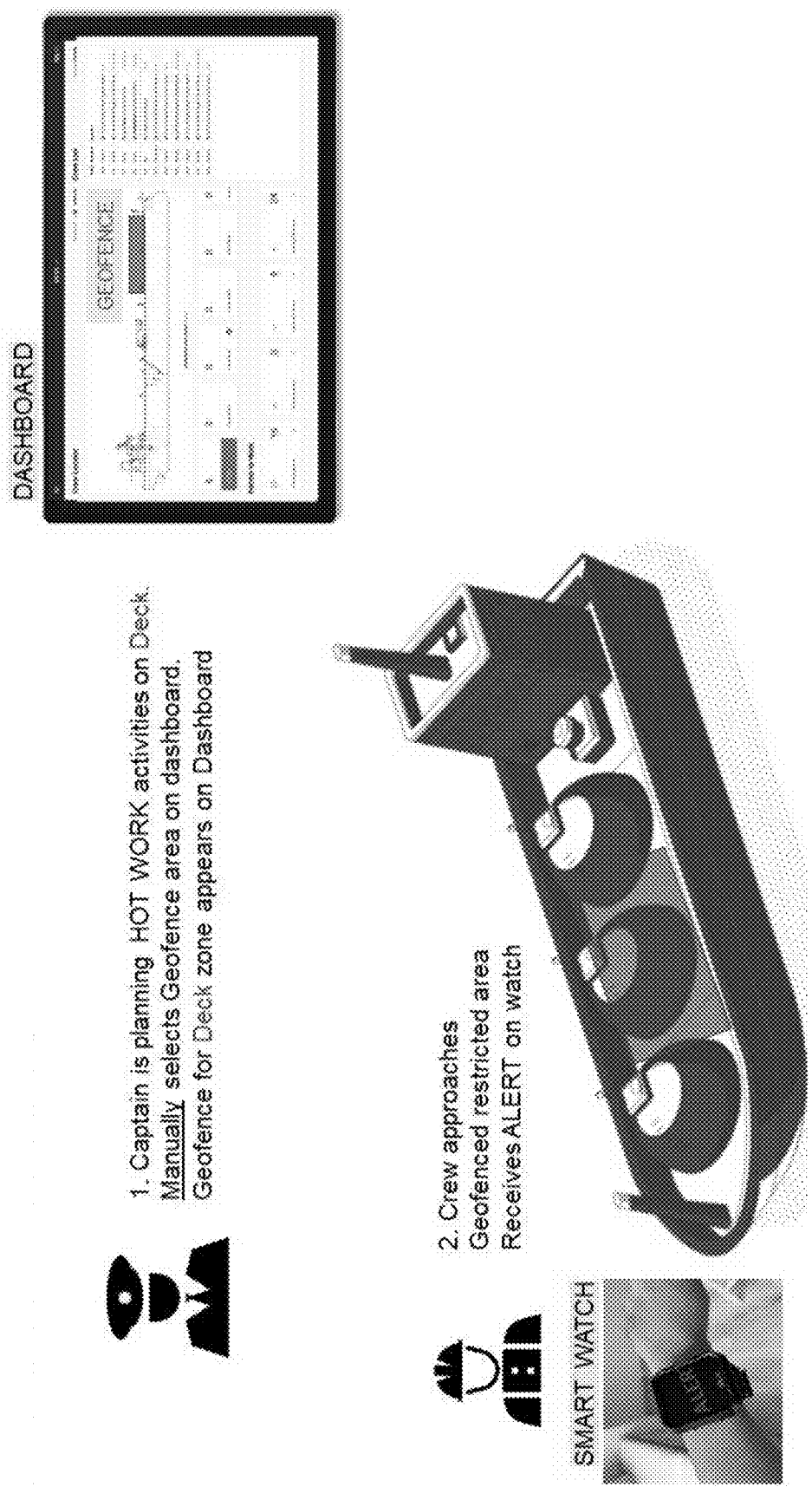
FIG. 22 shows an example of generating and managing geofencing with fixed barrier using the system.

FIG. 22 shows an example of generating and managing geofencing with fixed barrier using the system. In the illustrated example, there are a few areas (e.g., Pump Room, Engine Control Room, etc.) on the shipping vessel that require an active geofence to exist at all times (e.g., 24 hours a day and 7 days a week).

In some cases, an individual may obtain an active permit for entering a geofencing area such as Pump room. If a pump room entry permit is active, workers can enter the Pump Room, as long as they record entry at Pump Room Entry dashboard. While the pump room entry permit is active and workers do not record entry while entering the Pump room, a breach of geofence is detected and the worker may be alerted via audio, vibration, visual and textual based alerts on their wearable device and/or supervisory dashboard for officers/watch keepers. When a pump room entry permit is not active, a breach of geofence may be detected with or without recording an active permit. The feedback can be in any suitable form in addition to an alert delivered through the wearable device or the alert to the supervisory dashboard. For example, if there is detection of breach, other workers close to the geofencing area may be notified to intercept the breacher.

The barrier management unit of the system may also permit users to manually modify or define a barrier at any given time. Officers/watch keepers plans a high hazard work that does not require permit to work. For example, officers/watch keepers may create a geofence on the supervisory dashboard by selecting zone(s) of the ship that need to be included in the geofence. Additional labels and details may be added to the geofence related to the duration of geofence, permit of work, permission to enter assigned to selected individuals or healthiness requirement associated with the area, and various others. The duration of the geofence can also be terminated by the officers/watch keepers at any given time via the dashboard.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for managing safety and risk in a remote workplace comprising:
   (a) collecting, via a local network deployed to the workplace that is on a movable object, data stream from one or more sensors and a user device, wherein a geo-location of the local network is detected and wherein a data transmission scheme between the local network and a cloud server is determined based at least in part on the geo-location, and wherein the data transmission scheme specifies which portion of the data stream to be transmitted from the local network to the cloud server, a data center, a cloud database and a third party entity, when and at what frequency to transmit the portion of the data stream;

(b) transmitting, via the local network, the data stream to an edge computing device located within the workplace, wherein the data stream is stored in a database local to the workplace;

(c) processing the data stream as input by one or more trained predictive models running on the edge computing device, and outputting (i) a predicted hazardous condition associated with a work zone within the workplace and (ii) a predicted health condition of a user associated with the user device, wherein the one or more predictive models are trained and developed using machine learning algorithm at an entity remote from the workplace; and (d) generating a dynamic geofencing area associated with the work zone, wherein the dynamic geofencing area is generated by adjusting a boundary of the dynamic geofencing area base at least in part on the predicted hazardous condition, and determining a permitted duration for the user to be in the dynamic geofencing area based at least in part on the predicted health condition.

2. The method of claim 1, wherein the one or more sensors comprise at least one first sensor located onboard the user device and at least one second sensor deployed in the workplace.

3. The method of claim 2, wherein the user device is a wearable device and the data stream collected from the at least one first sensor located onboard the user device includes a heart rate of the user.

4. The method of claim 3, wherein the data stream collected from the at least one first sensor located onboard the user device further comprises an activity level of the user.

5. The method of claim 4, further comprising calculating a work and rest hour of the user based on the data stream.

6. The method of claim 3, wherein the data stream collected from the at least one first sensor located onboard the user device includes a temperature and humidity of an environment surrounding the user.

7. The method of claim 6, further comprising determining a heat stress level of the user based on the data stream.

8. The method of claim 1, wherein the predicted hazardous condition includes a predicted impeding hazardous event that occurs within a timespan of the predicted hazardous condition.

9. The method of claim 1, wherein the predicted health condition of the user comprises a fatigue level or a heat stress level.

10. The method of claim 1, wherein the permitted duration for the user to be in the dynamic geofencing area is further determined based at least in part on an operation to be performed within the geofencing area.

11. The method of claim 1, wherein a permission to enter the dynamic geofencing area is determined based at least in part on the predicted health condition of the user.

12. The method of claim 1, wherein a permission to enter the dynamic geofencing area is determined by a supervisory user and the dynamic geofencing area is automatically terminated upon detection of an operation completed within the geofencing area.

13. The method of claim 1, further comprising transmitting, via a gateway device, a report comprising the predicted hazardous condition and the predicted health condition, and at least a portion of the data stream using the data transmission scheme to the cloud server for further analysis.

14. The method of claim 1, wherein the data transmission scheme is generated based on a set of rules.

15. A system for managing safety and risk in a remote workplace comprising:
a local network deployed in the workplace on a movable object, data stream from one or more sensors and a user device, and wherein a geo-location of the local network is detected and wherein a data transmission scheme between the local network and a cloud server is determined based at least in part on the geo-location, and wherein the data transmission scheme specifies which portion of the data stream to be transmitted from the local network to the cloud server, a data center, a cloud database and a third party entity, when and at what frequency to transmit the portion of the data stream;
an edge computing device local to the workplace and configured to:
receive the data stream from the one or more sensors and the user device via the local network, wherein the data stream is stored in a database located within the workplace;
process the data stream as input by one or more trained predictive models running on the edge computing device, and output (i) a predicted hazardous condition associated with a work zone within the workplace and (ii) a predicted health condition of a user associated with the user device, wherein the one or more predictive models are trained and developed using machine learning algorithm at an entity remote from the workplace; and
generate a dynamic geofencing area in the work zone, wherein the dynamic geofencing area is generated by adjusting a boundary of the dynamic geofencing area based at least in part on the predicted hazardous condition, and determining a permitted duration for the user to be in the dynamic geofencing area based at least in part on the predicted health condition.

16. The system of claim 15, wherein the one or more sensors comprise at least one first sensor located onboard the user device and at least one second sensor deployed in the workplace.

17. The system of claim 16, wherein the user device is a wearable device and the data stream collected from the at least one first sensor located onboard the user device includes a heart rate of the user.

18. The system of claim 17, wherein the data stream collected from the at least one first sensor located onboard the user device further comprises an activity level of the user.

19. The system of claim 18, wherein the edge computing device is further configured to calculate a work and rest hour of the user based on the data stream.

20. The system of claim 16, wherein the data stream collected from the at least one first sensor located onboard the user device includes a temperature and humidity of an environment surrounding the user.

21. The system of claim 20, wherein the edge computing device is further configured to determine a heat stress level of the user based on the data stream.

22. The system of claim 15, wherein the predicted hazardous condition includes a predicted impeding hazardous event that occurs within a timespan of the predicted hazardous condition.

23. The system of claim 15, wherein the predicted health condition of the user comprises a fatigue level or a heat stress level.

24. The system of claim 15, wherein the permitted duration for the user to be in the dynamic geofencing area is further determined based at least in part on an operation to be performed within the geofencing area.

25. The system of claim 15, wherein a permission to enter the dynamic geofencing area is determined based at least in part on the predicted health condition of the user.

26. The system of claim 15, wherein a permission to enter the dynamic geofencing area is determined by a supervisory user and the dynamic geofencing area is automatically terminated upon detection of an operation completed within the geofencing area.

27. The system of claim 15, wherein the edge computing device is configured to further transmit, via a gateway device, a report comprising the predicted hazardous condition and the predicted health condition, and at least a portion of the data stream using the data transmission scheme to the cloud server for further analysis.

28. The system of claim 15, wherein the data transmission scheme is generated based on a set of rules.

* * * * *